(12) United States Patent
Vandroux et al.

(10) Patent No.: US 11,266,370 B2
(45) Date of Patent: Mar. 8, 2022

(54) METHODS AND SYSTEMS FOR OPERATING AN ELECTRONIC SYSTEM

(71) Applicant: GE Precision Healthcare LLC, Milwaukee, WI (US)

(72) Inventors: Stephane Vandroux, Paris (FR); Gauthier Libaux, Versailles (FR)

(73) Assignee: GE Precision Healthcare LLC, Milwaukee, WI (US)

( * ) Notice: Subject to any disclaimer, the term of this patent is extended or adjusted under 35 U.S.C. 154(b) by 176 days.

(21) Appl. No.: 16/775,011

(22) Filed: Jan. 28, 2020

(65) Prior Publication Data
US 2021/0228176 A1 Jul. 29, 2021

(51) Int. Cl.
*H05G 1/08* (2006.01)
*A61B 6/00* (2006.01)
(Continued)

(52) U.S. Cl.
CPC ............ *A61B 6/548* (2013.01); *A61B 6/0487* (2020.08); *A61B 6/42* (2013.01); *A61B 6/4441* (2013.01);
(Continued)

(58) Field of Classification Search
CPC ....... A61B 6/0487; A61B 6/42; A61B 6/4441; A61B 6/4452; A61B 6/461; A61B 6/467; A61B 6/548; A61B 6/586; A61B 6/4405; A61B 34/35; A61B 17/29; A61B 6/504; A61B 90/60; A61B 90/361; A61B 1/0638; A61B 34/37; A61B 34/74; A61B 90/06; A61B 34/30; A61B 6/4458; A61B 34/20; A61B 6/4476; A61B 2090/376; A61B 6/4429; A61B 90/50; A61B 6/54; A61B 6/06; A61B 6/08; A61B 6/4494; A61B 6/566; A61B 6/563; A61B 6/4014;
(Continued)

(56) References Cited

U.S. PATENT DOCUMENTS 6,785,578 B2 8/2004 Johnson et al.
6,925,578 B2 8/2005 Lam et al.
(Continued)

FOREIGN PATENT DOCUMENTS

EP 3051512 B1 11/2019
JP 5137327 B2 2/2013

*Primary Examiner* — Irakli Kiknadze
(74) *Attorney, Agent, or Firm* — McCoy Russell LLP

(57) ABSTRACT

In one example, an electronic system includes, a user interface comprising an input device, a first actuator and a second actuator, the first and second actuators dually actuated by the input device, and a controller, including a comparator, a programmable device, and executable instructions residing in non-transitory memory thereon to, receive first and second output signals from the first and second actuators, respectively, convert the first and second output signals to first and second real-time logic states at the comparator, input the first and second real-time logic states from the comparator to the programmable device, and determine a fault status of the first and second actuators based on the first and second logic states input to a state machine of the programmable device, wherein the first and second logic states input to the state machine include the real-time logic states and historical logic states stored at the controller.

20 Claims, 16 Drawing Sheets

(51) Int. Cl.
*G06F 30/34* (2020.01)
*H03K 19/0175* (2006.01)
*H03K 3/0233* (2006.01)
*A61B 6/04* (2006.01)

(52) U.S. Cl.
CPC ............ *A61B 6/4452* (2013.01); *A61B 6/461* (2013.01); *A61B 6/467* (2013.01); *A61B 6/586* (2013.01); *G06F 30/34* (2020.01); *H03K 3/02337* (2013.01); *H03K 19/017581* (2013.01)

(58) Field of Classification Search
CPC ......... A61B 5/055; A61B 8/40; A61B 6/5247; A61B 6/508; A61B 8/0825; A61B 5/4312; A61B 8/4416; A61B 5/0091; A61B 6/502; A61B 6/4417; A61K 41/0028; A61K 47/6849; A61K 9/0009; A61K 9/5115; B82Y 5/00; C07K 16/2896; C07K 2317/77; G06F 30/34; G06F 17/11; H01F 1/447; H03K 19/017581; H03K 3/02337; G16B 40/20; G16B 20/20; G16B 30/00; G06N 5/003; G06N 5/04; G06N 5/022; G16H 70/40; G16H 10/40; G16H 20/00; G16H 50/70; G16H 50/30; G16H 20/10; G16H 30/20; G16H 30/40; H01J 2237/2442; H01J 2237/28; G21K 1/02; A61N 5/1037; A61N 5/1039; A61N 5/103; A61N 5/1083; A61N 5/1049; A61N 5/1081; A61N 5/107; G01R 33/3802; G01R 33/3685
USPC ............................................................ 378/91
See application file for complete search history.

(56) References Cited

U.S. PATENT DOCUMENTS

| | | |
|---|---|---|
| 7,783,009 B2 | 8/2010 | Bielski et al. |
| 8,208,988 B2 | 6/2012 | Jensen |
| 2017/0353366 A1* | 12/2017 | Nasgowitz .............. H04L 41/22 |
| 2019/0059827 A1* | 2/2019 | Nye ....................... A61B 6/4035 |
| 2020/0093451 A1* | 3/2020 | Nett ........................ A61B 6/545 |
| 2020/0100758 A1* | 4/2020 | Viswanathan ......... A61B 6/587 |
| 2020/0360728 A1* | 11/2020 | Tilly .................... A61N 5/1036 |

* cited by examiner

FIG. 3
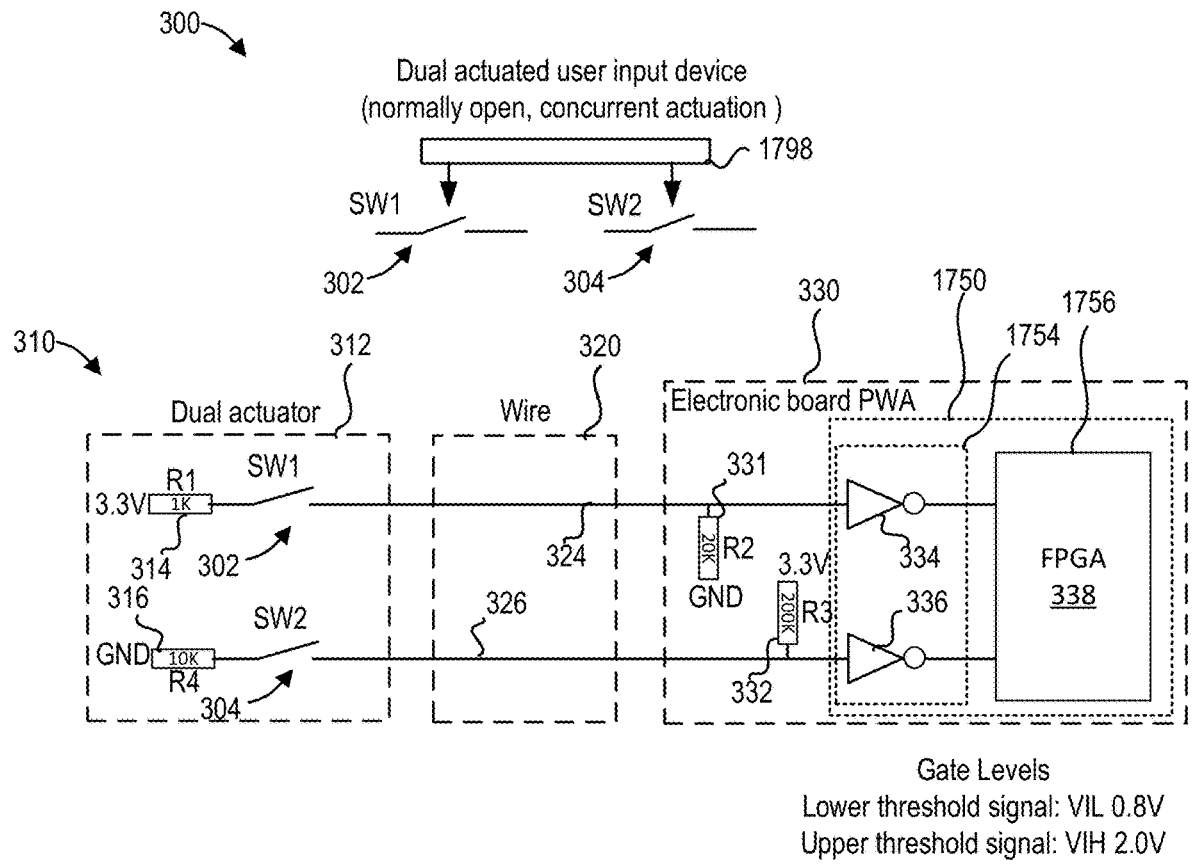
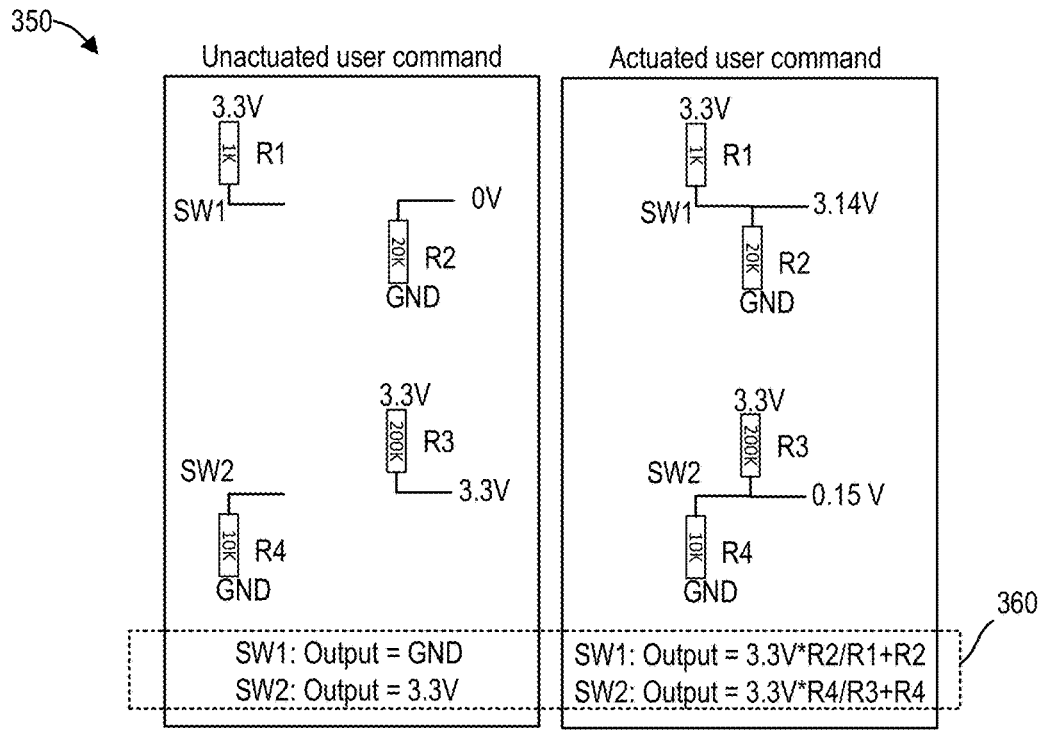

FIG. 4

| Normal operation | Error | User command state | Action state | Output average | Output min | Output max | Fault status | VIL | VIH | Logic state |
|---|---|---|---|---|---|---|---|---|---|---|
| SW1 | none | unactuated | OFF | 0 | 0 | 0 | OK | 0.8 | 2 | 0 |
| SW2 | none | unactuated | OFF | 3.3 | 3.3 | 3.3 | OK | 0.8 | 2 | 1 |
| SW1 | none | actuated | ON | 3.143 | 2.814 | 3.604 | OK | 0.8 | 2 | 1 |
| SW2 | none | actuated | ON | 0.157 | 0.128 | 0.176 | OK | 0.8 | 2 | 0 |

FIG. 5

| Stuck actuator | Error | User command state | Action state | Output average | Output min | Output max | Fault status | VIL | VIH | Logic state |
|---|---|---|---|---|---|---|---|---|---|---|
| SW1 | none | actuated | ON | 3.143 | 2.814 | 3.46 | OK | 0.8 | 2 | 1 |
| SW2 | stuck open | actuated | OFF | 3.3 | 3.3 | 3.3 | ERROR | 0.8 | 2 | 1 |
| SW1 | stuck open | actuated | OFF | 0 | 0 | 0 | ERROR | 0.8 | 2 | 0 |
| SW2 | none | actuated | ON | 0.157 | 0.128 | 0.176 | OK | 0.8 | 2 | 0 |
| SW1 | none | actuated | ON | 3.143 | 2.814 | 3.46 | OK | 0.8 | 2 | 1 |
| SW2 | stuck closed | actuated | ON | 0.157 | 0.128 | 0.176 | No error detected | 0.8 | 2 | 0 |
| SW1 | stuck closed | actuated | ON | 3.143 | 2.814 | 3.46 | No error detected | 0.8 | 2 | 1 |
| SW2 | none | actuated | ON | 0.157 | 0.128 | 0.176 | OK | 0.8 | 2 | 0 |
| SW1 | none | unactuated | OFF | 0 | 0 | 0 | OK | 0.8 | 2 | 0 |
| SW2 | stuck open | unactuated | OFF | 3.3 | 3.3 | 3.3 | No error detected | 0.8 | 2 | 1 |
| SW1 | stuck open | unactuated | OFF | 0 | 0 | 0 | No error detected | 0.8 | 2 | 0 |
| SW2 | none | unactuated | OFF | 3.3 | 3.3 | 3.3 | OK | 0.8 | 2 | 1 |
| SW1 | none | unactuated | ON | 0.157 | 0.128 | 0.176 | OK | 0.8 | 2 | 0 |
| SW2 | stuck closed | unactuated | ON | 3.143 | 2.814 | 3.46 | ERROR | 0.8 | 2 | 1 |
| SW1 | stuck closed | unactuated | ON | 3.3 | 3.3 | 3.3 | ERROR | 0.8 | 2 | 1 |
| SW2 | none | unactuated | OFF | 3.3 | 3.3 | 3.3 | OK | 0.8 | 2 | 1 |

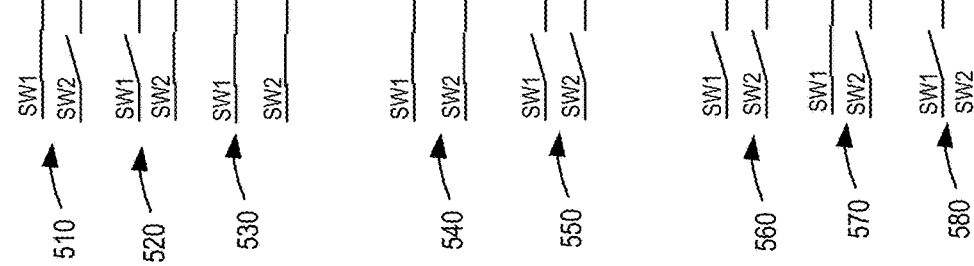

FIG. 8

| Short circuit to VCC | Error | User command state | Action state | Output average | Output min | Output max | Fault status | VIL | VIH | Logic state |
|---|---|---|---|---|---|---|---|---|---|---|
| SW1 | short circuit to VCC | unactuated | OFF | 3.3 | 3.3 | 3.3 | ERROR | 0.8 | 2 | 1 |
| SW2 | none | unactuated | OFF | 3.3 | 3.3 | 3.3 | OK | 0.8 | 2 | 1 |
| SW1 | short circuit to VCC | actuated | ON | 3.3 | 3.3 | 3.3 | No error detected | 0.8 | 2 | 1 |
| SW2 | none | actuated | ON | 0.157 | 0.128 | 0.178 | OK | 0.8 | 2 | 0 |
| SW1 | NO | unactuated | OFF | 0 | 0 | 0 | OK | 0.8 | 2 | 0 |
| SW2 | short circuit to VCC | unactuated | OFF | 3.3 | 3.3 | 3.3 | No error detected | 0.8 | 2 | 1 |
| SW1 | NO | actuated | ON | 3.3 | 3.3 | 3.3 | OK | 0.8 | 2 | 1 |
| SW2 | short circuit to VCC | actuated | ON | 3.3 | 3.3 | 3.3 | ERROR | 0.8 | 2 | 1 |

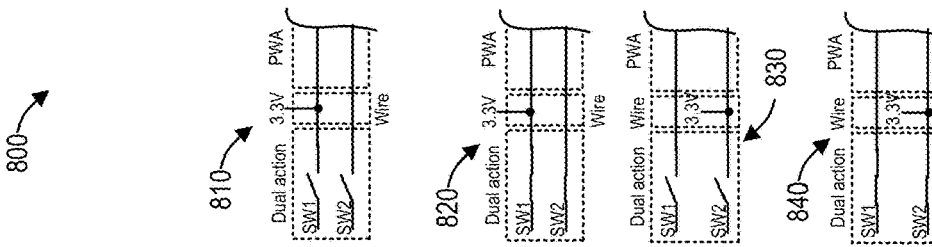

METHODS AND SYSTEMS FOR OPERATING AN ELECTRONIC SYSTEM

FIELD

Embodiments of the subject matter disclosed herein relate to systems and methods for electronic systems including a dually actuated input device.

BACKGROUND

Radiographic imaging systems may be used in medical and industrial applications as a less-invasive means to obtain images of an inner anatomy of a patient. Interventional radiology utilizes radiographic image-guided procedures to diagnose and treat internal organ ailments in real-time. Because the imaging and treatment procedures may be conducted concurrently in vivo, industry standards (e.g., IEC 60601) mandate continuous activation and dual switches for interventional radiology control systems. For example, in order to execute a control command, an operator may continually actuate a dually-actuated input device. Conventionally, fault tolerance in control systems can include providing dual redundant systems. For example, in computing systems, a duplicate set of devices, such as duplicate CPU's, switches, and/or nodes, and the like, may be incorporated into a system; as such, in the case where one set of hardware fails, data transmission may be preserved by utilizing the redundant set of devices. For dual switch control systems, such as those utilized in interventional radiology, fault tolerance is generally lacking; during conditions where one of the dually activated switches fail, the control command outright fails to execute.

The inventors have recognized potential issues with the above approaches. Namely, providing for redundant hardware systems is expensive, and increases system complexity. Furthermore, housing dual redundant hardware can be unwieldy and cumbersome especially in settings such as operating and surgery suites where dual switch control systems for medical technologies may be employed. Further still, in the absence of fault tolerance, dual switch controls may outright fail even when only one of the dual switches experiences a fault or error, including transient errors due to causes such as intermittent power fluctuations, electromagnetic interference, deteriorating wire connections, short circuits, and the like. For dual switch control systems employed in more sensitive applications such as interventional radiology, outright failure of the control system can have medically undesirable consequences since the failure may occur during real-time imaging and treatment of a patient. Further still, the severity of these undesirable consequences can far outweigh the risk to the dual switch control system functionality, especially when a failure may be transient in nature.

BRIEF DESCRIPTION

In one embodiment, an electronic system includes a user interface comprising an input device, a first actuator and a second actuator, the first and second actuators dually actuated by the input device, and a controller, including a comparator, a programmable logic device, and executable instructions residing in non-transitory memory thereon to, receive first and second output signals from the first and second actuators, respectively, convert the first and second output signals to first and second real-time logic states at the comparator, input the first and second real-time logic states from the comparator to the programmable logic device, and determine a fault status of the first and second actuators based on the first and second logic states input to a state machine of the programmable logic device, wherein the first and second logic states input to the state machine include the real-time logic states and historical logic states stored at the controller.

In this way the technical effect of increasing fault tolerance of a dually actuated control system as compared to conventional systems may be achieved. Furthermore the increased fault tolerant dually actuated control system may be provided without having a control system with dually redundant control hardware, thereby avoiding increased system complexity and cost. Further still, the electronic system described herein includes a method of assessing a severity and type of a fault such that in the case of certain less-severe fault types, functionality of the control system can be maintained. As such, the robustness and fault tolerance of the electronic system can be increased relative to conventional systems. Moreover, in the case of medical systems such as control systems for interventional radiology imaging, increased robustness and fault tolerance can aid in reducing the occurrence and severity of medically undesirable consequences by reducing outright failures due to transient (less-severe) faults. Further still, a more robust fault tolerant control system can be provided while maintaining compliance with industry standards.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 3 shows a schematic diagram and corresponding wiring diagram of an exemplary electronic system including a dually actuated device and control system therefor.

FIG. 4 shows a data table and wiring diagrams for normal operating modes of the electronic system of FIG. 3.

FIGS. 5-9 show data tables and wiring diagrams for faulty operating modes of the electronic system of FIG. 3.

DETAILED DESCRIPTION

The following description relates to various embodiments of a system and methods for operating an electronic system including a dually actuated device. An example electronic system is generically depicted in FIG. 17, and specific examples of the generic electronic system are depicted by the schematic and block diagrams of in FIGS. 2 and 3 for an interventional radiology imaging system, according to one embodiment. Operation of the electronic system including normal and error modes of the dually actuated device is represented by the schematics, data tables, and wiring diagrams depicted in FIGS. 3-9. Control and operation of the electronic system is aided by the truth table shown in FIG. 10, whereby truth table output logic states and an associated state machine, illustrated in FIG. 10, are referenced by a controller of the electronic system. Methods of operating the electronic system are represented by the flow charts of FIGS. 12-16.

Figure 1:
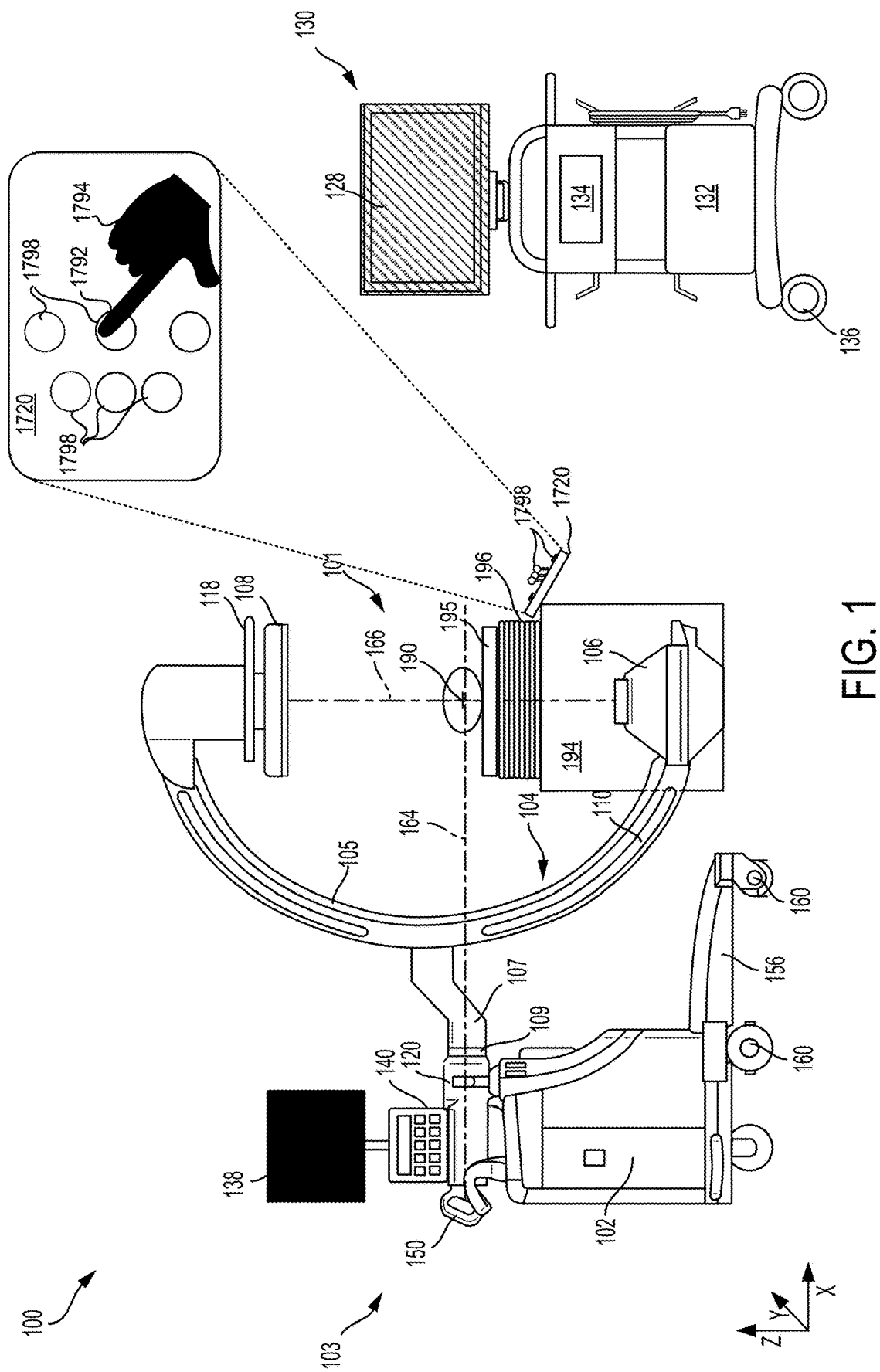
FIG. 1 shows an example of a mobile x-ray imaging system.
Figure 2:
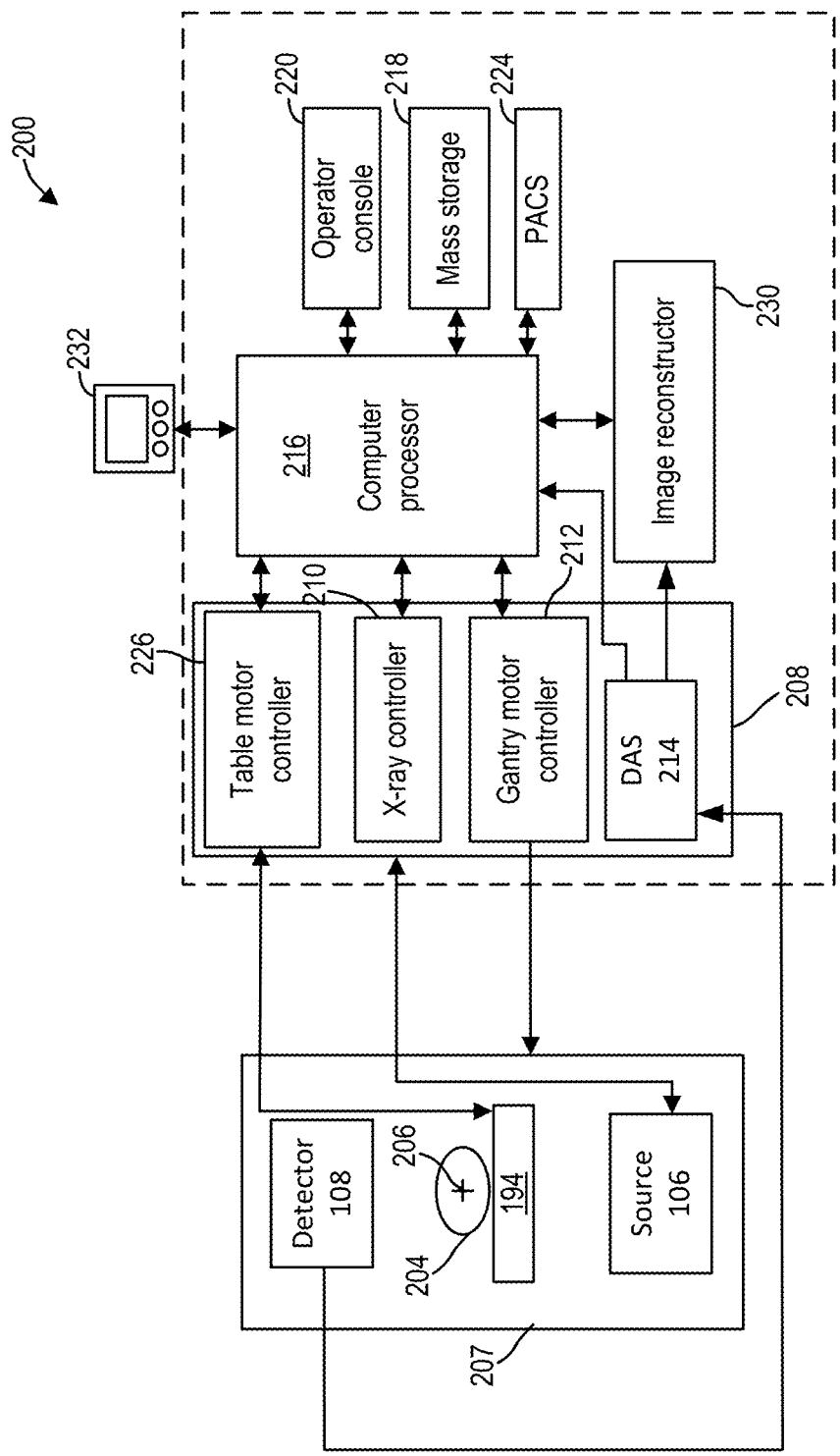
FIG. 2 shows a block schematic diagram of an exemplary imaging system.
Figure 17:
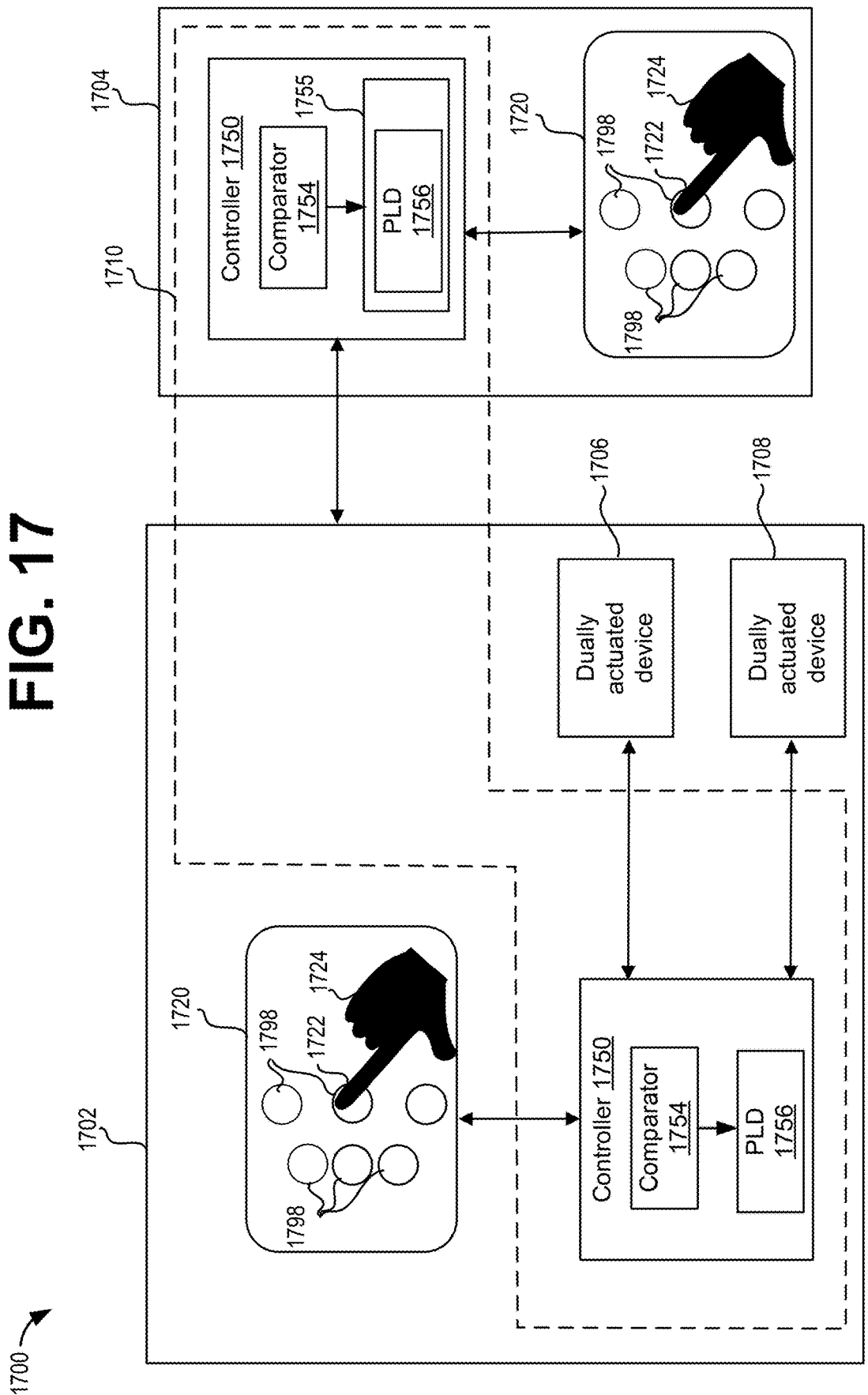
FIG. 17 shows a generic block schematic diagram of the exemplary electronic system of FIG. 3.

FIGS. 1, 2, and 17 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Turning now to FIG. 17, it illustrates a generic block diagram of an electronic system 1700, including one or more dually actuated devices 1706 and 1708, a control system 1710. The electronic system 1700 may include main local device 1702 as well as a remote or edge device 1706. As an example, the remote or edge device 1706 may allow for operation or control of the electronic system remotely by a user. Each of the main and remote devices 1702 and 1706 may include a controller 1750 and a user interface 1720, including one or more input devices 1798. In this way, the control system 1710 may be distributed across the main and remote devices 1702 and 1704, enabling local and remote control of the dually actuated devices 1706 and 1708. The one or more input devices 1798 are accessible to receive input from a user 1724, and are electronically coupled to dual actuators (not shown in FIG. 17, see FIG. 3) such that in response to receiving input, such as user input 1722, at an input device 1798, dual output signals corresponding to the dual actuators may be received at the controller 1710 for actuating a dually actuated device 1706, as described further herein with reference to FIG. 3. The input devices 1798 may include any type of input device, such as but not limited to a button, dial, switch, lever, joystick, keypad, touchpad, and the like. Thus, in normal (non-faulty) operating mode, actuating the input device, in turn, actuates the dual actuators, and thereby enables operation of the dually actuated device 1706.

The electronic system 1700 can include any electronic system utilizing a dual actuated input device. For example, with reference to FIGS. 2-3, the electronic system 1700 may include a medical imaging system such as an interventional radiology imaging system, wherein the input devices 1798 may receive user input 1722 for continuously activated dual-actuated motion control of the imaging system, including but not limited to, motion control of the gantry 207, patient table 194, lift, and the like. The input devices 1798 may receive user input 1722 for executing various other functions such as powering ON/OFF one or more subsystems of the electronic system 1700, modifying the displayed image (e.g., zoom, focus, start/stop image scan, storing the image, and the like), setting imaging parameters (e.g., radiation dosage, frequency, scan rate, scan power, field of view, and the like).

In other examples, the electronic system 1700 may include electronic systems other than medical electronic systems, where the user interface 1720 with input devices 1798 may include a keypad for a microwave oven, a TV remote, a touchscreen or keypad for a mobile communication device, an operator console for operating heavy machinery or construction vehicles (e.g., crane, gantry, CNC machinery, forklift, and the like), an elevator button array, a driver console for an electric or hybrid vehicle, personal computing input devices (e.g., keyboard, touchpad, mouse, and the like), an operator console for a building security alarm system, buttons and keys for electronic musical instruments, buttons/levers/touch pads for electronic toys and games, and the like. In this way, the methods and systems described herein may be utilized for incorporating increased fault tolerance and reliability in operation of a broad range of electronic systems.

The controller 1750 includes a comparator 1754 and a programmable logic device (1756). Controller 1750 may further include a power source, non-transitory and transitory memory, processors, and other electronic components. Upon receiving the dual output signals transmitted from the dual actuators, the controller 1750 may input the dual output signals to the comparator 1754. The comparator 1754 may include one or more of a number of electronic devices that compare two analog input signals and outputs a digital signal based on the relative magnitudes of the two analog input signals. As such, the comparator 1754 may include one or more analog-to-digital converters, operational amplifiers, and the like. In one embodiment, the comparator 1754 may include an inverter with a Schmitt trigger. In other embodiments, the comparator 1754 may include a non-inverted logic cate and a Schmitt trigger. The Schmitt trigger may include a comparator circuit with hysteresis implemented by applying positive feedback to the noninverting input of the comparator. When the comparator 1754 includes an electronic component such as a Schmitt trigger, an amount of hysteresis may be integrated into the comparator 1754 operation to aid in reducing a sensitivity of the comparator to output signal noise transmitted from the dual actuators, and thereby increase reliability of the comparator 1754. A digital signal may be output from the comparator 1754 for each of the dual output (analog) signals received by the comparator 1754 from the dual actuators. In one example, each of the dual output signals transmitted from the dual actuators may be input into a separate comparator 1754; thus, each of the dual digital signals output from the two comparators 1754 may correspond to one of the dual actuators. The dual digital signals output from the two comparators 1754 may be referred to as logic states. Furthermore, as described herein with reference to FIGS. 3 and 10-16, the logic states output from the comparator 1754 may be input to a programmable device (PD) 1755. In the example of FIG. 17, the programmable device (PD) includes a programmable logic device (PLD) 1756. In other examples, the PD may include a microcontroller, a processor, PLD, and/or other type of programmable device.

In one embodiment, for the case where the PD includes PLD 1756, the PLD 1756 may include a field programmable gate array (FPGA). In other examples, the PLD 1756 may include one or more PLD's, including a programmable logic controller, logic gates, flip flops, relays, and FPGAs. The PLD 1756 may be configured to determine a fault status of each of the dual actuators based on one or more of the real-time logic states and the historical logic states corresponding to each dual actuator. Real-time logic states may refer to the current logic states obtained from converting the real-time output signals received from the dual actuators at the controller 1750. In contrast, historical logic states may refer to previous logic states stored in memory residing at the controller 1750, and obtained from converting the output signals received from the dual actuators at the controller 1750 at a time prior to receiving the real-time output signals.

In one embodiment, the controller 1750 may include executable instructions residing thereon to input the real-time and/or historical logic states to a state machine configured at the PLD 1756. As described below with reference to FIGS. 10 and 11, additional logic states, including an output logic state based on a truth table equation (e.g., a combination of the real-time and historical logic states corresponding to the dual actuators) may be input to the state machine configured at the PLD 1756. In other words, the PLD 1756 may determine a fault status of each of the dual actuators based on one or more of the real-time and historical logic states of the dual actuators, and the output logic state. Furthermore, the controller 1750 may execute specific operational actions in response to the fault status determined by the PLD 1756, as further described herein with reference to FIGS. 10-16.

Turning to FIG. 1, it illustrates an example embodiment of the generic electronic system 1700, an imaging system 100. In particular, FIG. 1 shows a side view of the imaging system 100, having a C-arm 104 with an x-ray source 106 (hereinafter also referred to as the source 106 positioned directly below an x-ray detector 108 (hereinafter also referred to as the detector 108). The imaging system 100 also includes a base console 103 (e.g., local device 1702) and a remote console 130 (e.g., remote device 1706) communicatively (e.g., wired and/or wirelessly) coupled to the base console 103, x-ray detector 108, x-ray source 106, and patient table 194. A base portion 156 of the base console 103 may include a plurality of wheels 160 that allow the imaging system 100 to be transported from one position to another. Each wheel 160 may include a brake that allows the wheel to be locked into a fixed position, to prevent movement of the imaging system 100.

As shown in FIG. 1, the C-arm 104 may include a C-shaped portion 105 connected to an extended portion 107 coupled to a cross member 120 via a rotatable joint 109. The cross member 120 may be mounted to the base console 103 which may provide support to the C-arm 104. A lock handle 150 may be adjusted to unlock the C-arm 104, to allow the C-arm to rotate via the rotatable joint 109. As an example, the C-arm 104 may be configured to rotate at least 180 degrees in each direction via the rotatable joint 109 coupling the C-shaped portion 105 to the extended portion 107 of the C-arm 104.

In one example, the C-arm 104 may be rotatable (via the rotatable joint 109) about a central axis 164 of the C-shaped portion 105, to adjust the x-ray source 106 and detector 108 (positioned on opposite ends of the C-shaped portion of the C-arm 104 along a vertical axis 166) through a plurality of positions (e.g., at least switch vertical positions, top and bottom, between the detector and x-ray source). The C-shaped portion 105 of the C-arm 104 may include a plurality of handle bars 110 that may be held when rotating the C-arm via the rotatable joint 109, to adjust positions of the x-ray source 106 and detector 108 before or during operation of the imaging system 100. A curved handle 118, provided on the detector 108, may be used to adjust position of the detector 108 with respect to the x-ray source 106.

During an imaging operation, a portion of a patient's body 190 placed in a clearance (e.g., gap 101) formed between the x-ray source 106 and detector 108, may be irradiated with radiation from the x-ray source 106. The radiation may penetrate the portion of the patient's body 190 being irradiated, and travel to the detector 108 where the radiation is captured. By penetrating the portion of the patient's body 190 placed between the x-ray source 106 and detector 108, an image of the patient's body 190 is obtained and relayed to a first display monitor 128 via a connection line (e.g., wireless and/or wired electrical connection line) where the image is displayed or stored and retrieved later. In one example, the first display monitor 128 may display images taken and processed by the imaging system 100, as they are taken and during the imaging procedure (e.g., in real-time). Real-time imaging may further allow for utilization of the imaging system 100 in interventional radiology procedures whereby not only imaging, but also treatment of a patient (e.g., laparoscopic surgical procedures, in vivo drug delivery, and the like) may be concurrently performed. Display monitor 128 may also include an operator console, whereby user commands may be input by a user via the display monitor 128.

The patient's body 190 may be supported by a patient table 194 including a supporting portion 195 in contact with the patient's body and an adjustable portion 196 which may be tilted, translated, expanded, contracted, and the like, in the x-, y-, and/or z-directions, in order to appropriately position the patient's body 190 for imaging and/or for performing interventional procedures thereat. A user interface 1720 may be provided at the patient table, including one or more input devices 1798 (e.g., buttons, levers, switches, and the like) for electronically positioning the surface of the supporting portion 195 and the patient's body 190. The one or more input devices 1798 may further include controls for electronically positioning the x-ray detector 108 relative to the x-ray source 106 through positioning (translation, rotation, and the like) of C-arm 104. As described above with reference to FIG. 17, the input devices 1798 may activate dual actuators upon receiving user input 1722 thereat for motion control of the C-arm 104 and/or patient table 194.

According to industry standards (e.g. IEC 60601), the controls for imaging system 100 may include continuous activation and dual actuation. Continuous activation refers to uninterrupted actuation of an input device for enabling electronic control. For example, a user may reposition the C-arm 104 only by continuously activating the corresponding input device(s). For instance, in the case where the input device 1798 is a button to tilt the patient table 194, the user 1794 may tilt the patient table 194 only while continuously pushing a button; releasing the button stops the motion control of the patient table 194. Dual actuation may refer to an input device 1798 actuating dual actuators, whereby each of the dual actuators transmits an output signal to the control system 1752. The control system 1752 can assess the fault status of the dual actuators based on the values of their output signals. As described with reference to FIG. 3 herein, upon receiving the output signals transmitted from the dual actuators, the controller may convert those output signals to logic states, which can aid in assessing the operational state of the dual actuated input device 1798. A control system relying on the robustness of two output signals may provide higher reliability as compared to a single actuated system with a single output signal.

Remote console 130 may include the first display monitor 128 as a separate unit from the C-arm 104 and other components attached to the C-arm 104. The first display monitor 128 may be mounted on the remote console 130, which may further include a computing unit 132. The computing unit 132 may be communicatively coupled to the first display monitor 128 and may further communicate with a control and base computing unit 102 arranged in the base console 103 of the imaging system via a communication cable or a wireless communication link. The computing unit 132 may be configured to display x-ray FOV previews and x-ray images obtained via the imaging system 100 at the first display monitor 128.

A first user interface 134 (e.g., input device) may be included in the remote console 130, and may include a plurality of input devices used to input commands to control or adjust display of the x-ray images. The first user interface 134 may be analogous to user interface 1720, as previously described. The remote console 130 may be implemented on wheels 136 to allow the remote console 130 to be readily repositioned relative to a user and to the C-arm 104. As such, the remote console 130 may be positioned next to a surgeon operating on and/or treating a patient. The surgeon's view of the first display monitor 128 may be adjusted as desired by moving the remote console 130. Furthermore, through the first user interface 134, a user may electronically control a position of the C-arm 104 and patient table 194, and other electronic control functions accessible at base console 103 and/or user interface 1720.

In some examples, the imaging system 100 may include more than one display monitor. For example, a second display monitor 138 may be positioned above the base computing unit 102. The second display monitor 138 may be fixedly attached to the cross-member 120 and may also display x-ray field-of-view (FOV) previews. In some examples, the second display monitor 138 may be configured to show a same display as the first display monitor 138. In other examples, the second display monitor 138 may be positioned to enable an operator of the imaging system 100 to view x-ray FOV previews and resulting x-ray images and manipulate and adjust the view independent of the first display monitor 138. Manipulation and adjustment of images displayed on the second display monitor 138 may be provided by a second user interface 140. Second user interface 140 (e.g., input device) may be analogous in function and content to first user interface 134 and user interface 1720. As such, second user interface may include a plurality of input devices 1798 for activating dually actuated continuously activated control actions (e.g., motion control of the imaging system 100).

The base console 103 may include the base control and the base computing unit 102 that processes instructions or commands sent from the first input device 134 and or the second input device 140 of the imaging system 100 during operation of the imaging system 100. The base computing unit 102 may also include an internal power source (not shown) that provides electrical power to operate the imaging system 100. Alternatively, the base computing unit 102 may be connected to an external electrical power source to power the imaging system 100. The x-ray source 106, detector 108, the computing unit 132 in the remote console 130, and the base control and the base computing unit 102 may communicate via a plurality of connection lines, for example, the plurality of connection lines enabling transmission of instructions and data. In alternative examples, input commands and data may be transmitted between the x-ray source 106, detector 108, and the base computing unit 102 via a wireless connection or network, thereby advantageously obviating the need for connection lines or cables.

In this way, the imaging system 100 may comprise: the base console 103; the remote console 130, the C-arm 104 coupled to the base console 103 and including an x-ray source 106 and detector 108 positioned on opposite ends of a C-shaped portion 105 of the C-arm 104; and one or more display monitors, e.g., the first display monitor 128 and the second display monitor 138.

FIG. 2 illustrates a generalized example of an imaging system 200. In accordance with aspects of the present disclosure, the imaging system 200 is configured for imaging a subject 204 (e.g., the patient's body 190 of FIG. 1). In one embodiment, the imaging system 200 includes the radiation detector 108 (see FIG. 1). The radiation detector 108 further may include a plurality of detector elements that together sense the radiation delivered from a radiation source 106 (see FIG. 1) that pass through the subject 204 (such as a patient) to acquire corresponding projection data. Accordingly, in one embodiment, the radiation detector 108 is fabricated in a multi-slice configuration including the plurality of rows of cells or detector elements (CT, MRI scanning). In such a configuration, one or more additional rows of the detector elements are arranged in a parallel configuration for acquiring the projection data.

In certain embodiments, the imaging system 200 is configured to traverse different angular positions around the subject 204 for acquiring desired projection data. Accordingly, the gantry 207 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle. Gantry 207 may include a C-arm type gantry as described with reference to FIG. 1. In other embodiments, the gantry 207 may include an annular gantry (e.g., CT scanner), a cylindrical gantry (e.g., Mill gantry), and other geometries. Furthermore, during the imaging process, the gantry 207 may be positioned to partially and/or completely surround the subject 204.

As the x-ray source 104 and the detector 108 move, the detector 108 collects data of the attenuated x-ray beams. The data collected by the detector 108 undergoes pre-processing and calibration to condition the data to represent the line integrals of the attenuation coefficients of the scanned subject 204. The processed data are commonly called projections.

In some examples, the individual detectors or detector elements of the detector 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 207 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 207 based on imaging requirements; and a table motor controller 226 for manipulating and positioning patient table 194.

In certain embodiments, the control mechanism 208 further includes a data acquisition system (DAS) 214 configured to sample analog data received from the detector 108 and convert the analog data to digital signals for subsequent processing. In this way, DAS 214 may further include electronic components such as the comparator 1754 for converting analog signals output by dually actuated input devices associated with the various actuators of the imaging system such as those controlled by table motor controller 226, x-ray controller 210, and/or gantry motor controller 212, as described with reference to FIG. 17. The DAS 214 may be further configured to selectively aggregate analog data from a subset of the detector elements 202 into so-called macro-detectors, as described further herein. The data sampled and digitized by the DAS 214 is transmitted to a computer processor 216. In one example, the computer processor 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computer processor 216 provides commands and parameters to one or more of the DAS 214, the x-ray controller 210, table motor controller, and the gantry motor controller 212 for controlling system operations such as motion control, and data acquisition and/or processing. In certain embodiments, the computer processor 216 controls system operations based on operator input. The computer processor 216 receives the operator input, for example, including commands and/or scanning parameters via an operator console 220 (e.g., user interface 1720) operatively coupled to the computer processor 216. The operator console 220 may include a keyboard (not shown), touchscreen, and other various user input devices 1798, to allow the operator to specify various control commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally (e.g., base console 103) or remotely (e.g., remote console 130), for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computer processor 216 uses the operator-supplied and/or system-defined commands and parameters to operate a table motor controller 226, which in turn, may control a table 228 which may be a motorized table, such as patient table 194. Specifically, the table motor controller 226 may move the table 228 for appropriately positioning the subject 204 in the gantry 207 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computer processor 216. Alternatively, the image reconstructor 230 may be absent from the imaging system 200 and instead the computer processor 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computer processor 216 for generating useful patient information for diagnosis and evaluation. In certain embodiments, the computer processor 216 may transmit the reconstructed images and/or the patient information to a display or display device 232 communicatively coupled to the computer processor 216 and/or the image reconstructor 230. In some embodiments, the reconstructed images may be transmitted from the computer processor 216 or the image reconstructor 230 to the storage device 218 for short-term or long-term storage.

The various methods and processes (such as the method described below with reference to FIGS. 12 through 16) described further herein may be stored as executable instructions in non-transitory memory on the computer processor 216, control mechanism 208, and/or image reconstructor 230 of the imaging system 200. As such devices such as the PLD 1756 may be included at one or more of the control mechanism 208 or at the computer processor 216 for receiving digital logic states converted at the DAS 214 from output signals transmitted by the various dually actuated input devices. In one embodiment, the image reconstructor 230 may include such executable instructions in non-transitory memory, and may apply the methods described herein to reconstruct an image from scanning data. In another embodiment, computer processor 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230, the control mechanism 208, and/or the computer processor 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

Turning now to FIG. 3, it illustrates a schematic of an example embodiment of a dual actuated input device 300, including the input device 1798. As described with reference to FIG. 17, the input device 1798 include any type of input device, such as but not limited to a button, dial, switch, lever, joystick, keypad, touchpad, and the like. As illustrated in FIG. 3, the input device 1798, when activated by a user, concurrently actuates first and second actuators 302 and 304. Concurrently actuating the first and second actuators 302 and 304 may include actuating one of the first and second actuators 302 and 304 then subsequently actuating the other of the first and second actuators 302 and 304 after a threshold delay. In one example, the threshold delay may include 1.5 s or shorter. The threshold delay may vary depending on the type and/or application of the electronic system 1700. In one example, the threshold delay may accommodate the inherent mechanical timing of the dual actuator system; in other words, waiting for a duration including the threshold delay can allow for both of the dual actuators to transition to a user-requested state in response to receiving the user input 1722 at the dual actuated device. In another example, in a medical imaging system, IEC standards may mandate that a threshold delay be less than a specified duration; in other types of electronic systems, shorter and/or longer durations may be desired. The first and second actuators 302 and 304 are depicted as switches (SW1 and SW2, respectively) for illustration, but SW1 and SW2 can include various types of actuators such as electrical, mechanical, pneumatic, electronic actuators, and the like. As indicated by the IEC60601-1 standard, SW1 and SW2 actuators can include a device having the capability of isolating an electrical input; which may or may not include a mechanical system. For example, the first and second actuators 302 and 304 may include a switch, relay, transistor, capacitor, microcontroller signal, resistor, and the like.

In response to activation of the input device 1798 by a user, the first and second actuators 302 and 304 change state. The unactuated states of both first and second actuators 302 and 304 are illustrated as OPEN (e.g., normally open); however, in other examples, the unactuated states of both first and second actuators 302 and 304 may be both CLOSED. Furthermore, the unactuated and/or actuated states of both first and second actuators 302 and 304 may be different or opposite states. For example, in other embodiments, the unactuated state of actuator 302 may be OPEN while the unactuated state of actuator 304 may be CLOSED (and vice versa); continuing with the example, it follows that the (normal) actuated state of first and second actuators 302 and 304 is CLOSED and CLOSED, respectively. Thus, in the case where the input device 1798 is a button, upon pressing of the button, the first and second actuators 302 and 304 (depicted as switches) may change state from their respective unactuated states to their respective actuated states, during non-faulty (e.g., normal) operation.

The wiring diagram 310 illustrates an electronic embodiment of the dual actuator 312 (including first and second actuators 302 and 304) conductively coupled to a controller 330 by way of an electronic connector 320. As shown in wiring diagram 310, the first and second actuators 302 and 304 may include electronic components such has resistors R1 and R4, respectively. Although the wiring diagram 310 depicts resistors R1 and R4, the first and second actuators 302 and 304 may include other resistor configurations and/or configurations including resistors and/or other types of electronic components coupled to SW1 and SW2 to generate the desired characteristic output signals, including electronic components that may generate analog signals or electronic components that may be employed for digital to analog conversion. Electronic connector 320 includes wires 324 and 326 which conductively couple each of the first and second actuators 302 and 304 to an electronic board printed wire assembly (PWA) 330. The PWA 330 includes various electronic components such as additional resistors R2 and R3, and the controller 1750, which in turn includes comparators 1754, and a PLD 1756. In the wiring diagram 310, the comparators 1754 include a pair of inverters with Schmitt triggers 334 and 336, however in other examples, other types of comparator devices such as OPAMP, ADC, transistors, and the like, for converting analog signals to digital signals may be utilized. The wire 324 couples SW1 to the resistor R2 and first inverter (with Schmitt trigger) 334, while the wire 334 couples SW1 to the resistor R3 and second inverter (with Schmitt trigger) 336.

Both the first and second inverters 334 and 336 are connected to the PLD 1756. In the example of wiring diagram 310, the PLD 1756 includes an FPGA 338, however, in other embodiments, PLD 1756 may include other types of PLDs. The FPGA 338 may receive the digital signals output from the first and second inverters 334 and 336 corresponding to the first and second actuators 302 and 304, respectively. As described further herein, the FPGA may be configured to input the received digital signals to a state machine for determining a fault status of the first and second actuators 302 and 304. Furthermore, controller 1750 may include executable instructions residing in non-transitory memory thereat to calculate an output logic state based on real-time and historical logic states of the dual actuators 302 and 304; the output logic state and the logic states of the dual actuators may be input into a state machine configured at the PLD 1756 for indicating an error fault status at each of the dual actuators. Furthermore, responsive to the error fault status at each of the dual actuators, the controller 1750 may include executable instructions to maintain operation of the dual actuated input device 1798 during a normal mode condition including when an error fault status at each of the dual actuators is absent, maintain operation of the dual actuated input device 1798 during an error mode condition including when a fault status at one of the dual actuators is detected, maintain operation of the dual actuated input device 1798 during a degraded mode condition including when a fault status at one of the dual actuators persists beyond a threshold delay, and stop operation of the dual actuated input device 1798 during an inoperable condition including when a fault status at both of the dual actuators persists beyond the threshold delay. Each of the normal mode, error, degraded, and inoperable conditions of the dual actuated input device 1798 are described herein with reference to FIGS. 10-16.

The resistivities and arrangement (e.g., relative to SW1 and SW2) of resistors R1, R4, R2, and R3 may be chosen such that the first and second actuators 302 and 304 output signals that are characteristic of when they are respectively in their unactuated and actuated states, and that correspond to differentiable digital signals output by the comparators 1754 at the controller 1750, as described further herein. In the example of FIG. 3, R1 has a resistivity of 1 kOhm, R2 has a resistivity of 20 kOhm, R3 has a resistivity of 200 kOhm, and R4 has a resistivity of 10 kOhm. Also shown in FIG. 3 are example gate levels including a lower threshold signal, VIL, and an upper threshold signal, VIH, wherein VIL may be less than VIH. VIL and VIII may be input to the comparators 1754 (e.g., inverters 334 and 336) along with the output signals received from the first and second actuators 302 and 304. When an output signal is less than VIL, the inverter may output a first (digital) logic state; conversely, when the output signal is greater than VIH, the inverter may output a second (digital) logic state. Said another way, a logic state equivalent to the first logic state corresponds to the output signal from the corresponding actuator being less than VIL, whereas a logic state equivalent to the second logic state corresponds to the output signal from the corresponding actuator being greater than VIH. In the example of FIG. 3, the inverters 334 and 336 output a logic state of 1 when the output signal is greater than VIH, and output a logic state of 0 when the output signal is less than VIL.

VIL and VIH may be chosen according to the range of output signals transmitted when the first and second actuators are in their unactuated states and in their actuated states such that each of the first and second logic states can reliably be utilized to indicate via a digital signal, a state of the first and/or second actuators 302 and 304. Furthermore, the values of VIL and VIH, along with the configuration of other electronic components (e.g., resistors R1, R2, R3, and R4), may be selected such that during normal operation, the logic states corresponding to the first and second actuators are opposite and/or different when SW1 and SW2 are both in an actuated user command state (e.g., ON action state), or when SW1 and SW2 are both in an unactuated state (e.g., OFF action state), as described with reference to FIG. 4. In this way, the first and second logic states, when input to the FPGA 338, can then be used at least as a partial basis to aid in determining a fault status of the first and second actuators. In the example of FIG. 3, VIL is set at 0.8V and VIH is set at 2.0V.

The circuit schematic 350 illustrates the corresponding output signals for the first actuator (SW1) and the second actuator (SW2) when they are in an unactuated state and an actuated state. While unactuated (e.g., default state), SW1 transmits an output signal of 0V, and SW2 transmits an output signal of 3.3V; while actuated (e.g., in response to a user actuating input device 1798), SW1 transmits an output signal of 3.14V, and SW2 transmits an output signal of 0.15V, as calculated according to the output equations 360 shown in circuit schematic 350 for SW1 and SW2.

Table 400 (FIG. 4) shows the range of output signals transmitted by SW1 and SW2 when actuated and unactuated, during normal operation (without actuator faults or errors). As is evident from the entries of Table 400, a repeatable and reliable logic state is output for each of SW1 and SW2 when either actuator is in the unactuated or actuated state. For example, the range of output signals (e.g., from Output min to Output max) that are received from the first actuator during normal operation, is less than VIL when SW1 is unactuated. Additionally, the dual actuator circuits may be configured, for example, through judicious choice of resistors and other electronic components, such that VIL may be less than VIH by a threshold difference. The threshold difference between VIL and VIH can further increase reliability of outputting a repeatable and reliable output state for each of the dual actuators, by reducing a risk of error in outputting an inaccurate (misrepresentative) logic state.

As such, a logic state of 0 corresponding to the first actuator (e.g., a normal unactuated user command state of the first actuator) reliably indicates that SW1 is unactuated, during normal operation; similarly, a logic state of 1 corresponding to the first actuator (e.g., a normal actuated action state of the first actuator) reliably indicates that SW1 is actuated, during normal operation. Furthermore, a logic state of 1 corresponding to the second actuator (e.g., a normal unactuated action state of the second actuator) reliably indicates that SW2 is unactuated, during normal operation; similarly, a logic state of 0 corresponding to the second actuator (e.g., a normal actuated action state of the second actuator) reliably indicates that SW2 is actuated, during normal operation. Normal operation can further include when the actuator action state is consistent (e.g., equivalent) with the user command state in normal mode. In the case of FIG. 4, during normal operation, an action state is OFF (e.g., switch is OPEN) when the user command state is unactuated, and an action state is ON (e.g., switch is CLOSED) when the user command state is actuated.

In this way a control system can determine a faulty (e.g., non-normal) actuator from the logic states arising from output signals received from each actuator. When an actuator logic state for an actuated or unactuated actuator is different from its corresponding normal actuated logic state or normal unactuated logic state, respectively, an error may be indicated due to faulty operation of the actuator. Similarly, when an actuator action state for an actuated or unactuated actuator is different from its corresponding normal actuated action state or normal unactuated action state, respectively, an error may be indicated due to faulty operation of the actuator. Furthermore, in the case of a dual actuated input device 1798, equivalency and/or non-equivalency of the actuated logic states of each of the actuators may provide indication of the presence of an error in one or more of the actuators.

Turning now to FIGS. 5 through 9, they illustrate example data tables for the dual actuators corresponding to faulty actuator operation including errors arising from faults such as stuck actuators, short circuits, and open circuits. Stuck actuator, short circuit, and open circuit faults may be transient and intermittent, arising at least partially from intermittent power fluctuations, electromagnetic interference, deteriorating wire connections, and the like. As such, it may be advantageous to maintain operation of a dual actuated function even during conditions where a fault (e.g., error fault status) has been indicated for one of the dual actuators. Maintaining and allowing execution of a dual-actuated user command in the presence of a transient fault can reduce disruption of an electronic system's operation, especially when a fault status is transient and momentarily clears.

Data table 500 illustrates output signals and logic states arising from a single stuck actuator. A stuck actuator may correspond to a condition when an actuator fails to change state in response to a change in a user command state (e.g., from actuated to unactuated and vice versa). As an example, referencing the case 510 illustrated in Table 500, when SW2 is stuck OPEN, SW2 fails to CLOSE and its action state remains OFF, even in response to a change in user command state from an unactuated command state to an actuated user command state. Consequently, the logic state (e.g., 1) arising from the SW2 output signal is different from the normal actuated logic state of SW2, and an error fault status may be indicated for that actuator (SW2). Additionally, the error fault status may be indicated by the action state (e.g., OFF) being different from the normal actuated action state of SW2 (e.g., ON). Similarly, in data table 500, an error fault status for one of the dual actuators is indicated for cases 520, 570, and 580, responsive to when one of the actuators is stuck OPEN or stuck CLOSED, and a logic state and action state corresponding to the stuck actuator is different from its normal logic state corresponding to the user command state and normal action state corresponding to the user command state, respectively.

In the example of FIGS. 3-9, a logic state and an active state being different from its corresponding normal logic state and active state corresponds to the logic states for each of the dual actuators being equivalent (e.g., the logic states of SW1 and SW2 are both 1 or 0); this condition arises because the normal logic states and normal action states for the dual actuators are nonequivalent during normal operating conditions (FIGS. 3-4). For the cases 530, 540, 550, and 560, where one of the dual actuators is stuck OPEN or CLOSED, an error is not detected because the action state and the logic state of each actuator is equivalent with the normal action state and normal logic state corresponding to the user command state. Thus cases 530, 540, 550, and 560 illustrate conditions during which operation of the electronic system can proceed normally in spite of the stuck actuator because no error fault status is indicated.

Although not illustrated in data table 500, where both actuators are stuck, in the case where the logic states and action states of each actuator are equivalent with the normal logic states and normal action states, no error is detected; in the case where the logic states and action states of one of the actuators is not equivalent with its normal logic state and normal action state, an error fault status is indicated for that actuator; in the case where the logic states and action states of each of the dual actuators is different from its normal logic state and normal action state, an error fault status is indicated for both actuators. When an error fault status is indicated for both of the dual actuators, a major error is indicated, the user command is not executed, and operation of the electronic system is halted for repair and service.

Figure 6:
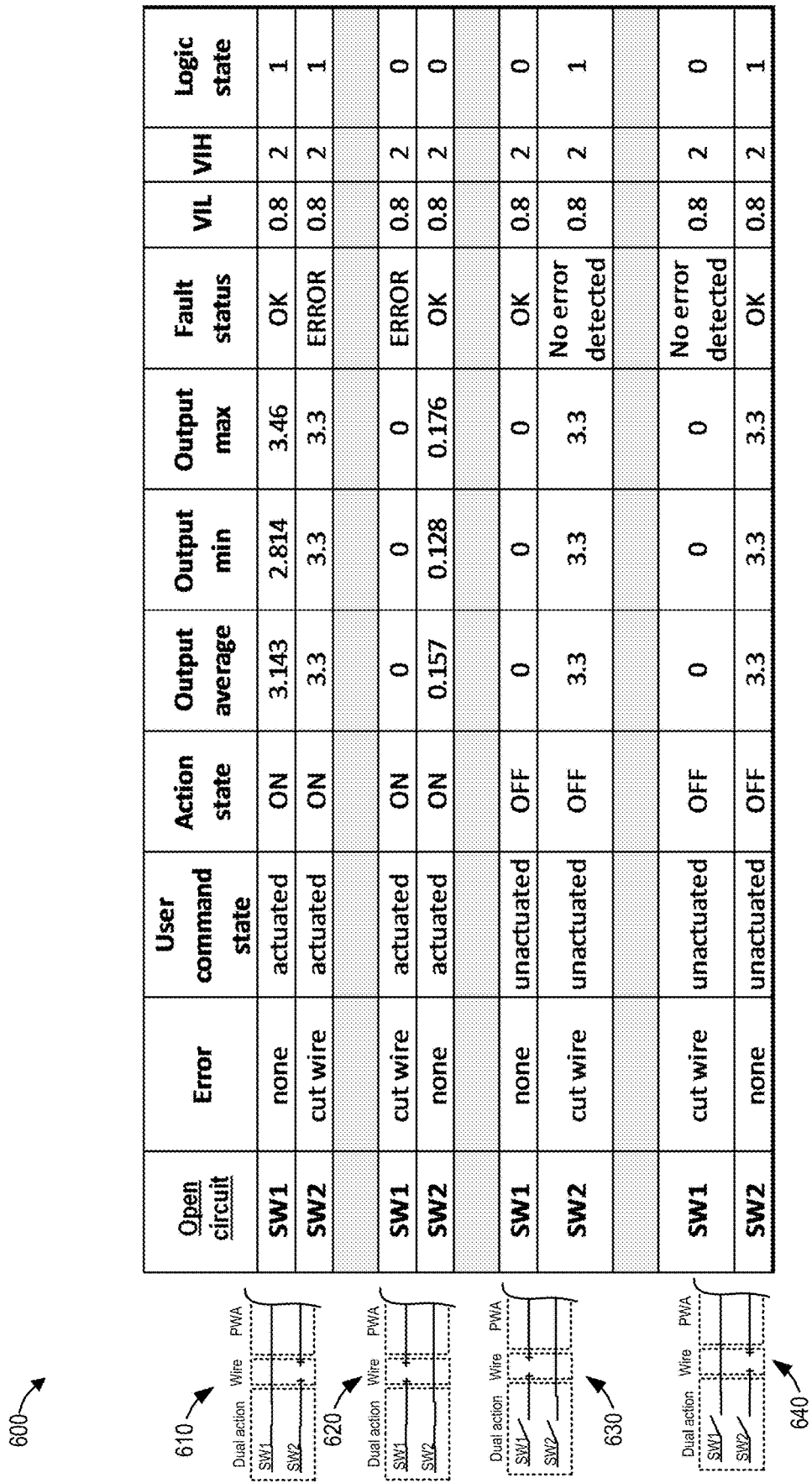

Turning now to FIG. 6, it shows a data table 600 illustrating output signals and logic states arising from open circuits. An open circuit may disrupt connectivity between one of the dual actuators (SW1 or SW2) and the PWA 330, and can arise, for example, from one of the circuit wires 320 connecting each of the dual actuators to the controller components may being severed or cut. In the case 610, an open circuit is caused by a discontinuity in wire 326 between the actuator SW2 and the PWA 330. As such, in response to a user command state actuating dual actuators SW1 and SW2 (e.g., receiving user input 1722 at an dual actuated input device), although the action state of SW2 is ON and equivalent with the normal actuated action state of SW2, an output signal (e.g., 3.3V) is transmitted to the controller that corresponds to a logic state of 1, which is different from the normal actuated logic state of 0 for SW2. In response the logic state being different from the normal actuated logic state, an error fault status is generated for the SW2 actuator. Case 1620 illustrates a similar condition where an error fault status is generated for the SW1 actuator due to a SW1 logic state differing from the normal SW1 logic state arising from a discontinuity in the wire 324 between the actuator SW1 and the PWA 330 during an actuated user command state.

In cases 630 and 640, the logic states arising from a discontinuity in a circuit between one of the dual actuators 302 and 304 and the PWA 330 during an unactuated user command state are equivalent with the normal logic states during an unactuated user command state, thus no error fault status is indicated for either dual actuator. Thus, cases 630 and 640 illustrate conditions during which operation of the electronic system can proceed normally in spite of the open circuit discontinuity in one of the dual actuator circuits because no error fault status is indicated.

Although not illustrated in table 600, in cases where there are discontinuities (e.g., open circuits) in both dual actuator circuits (e.g., between each dual actuator and the controller), no command is transmitted to the electronic connector 320 or controller 330; as such, a transition in the action states of the dual actuators is not detected.

Figure 7:
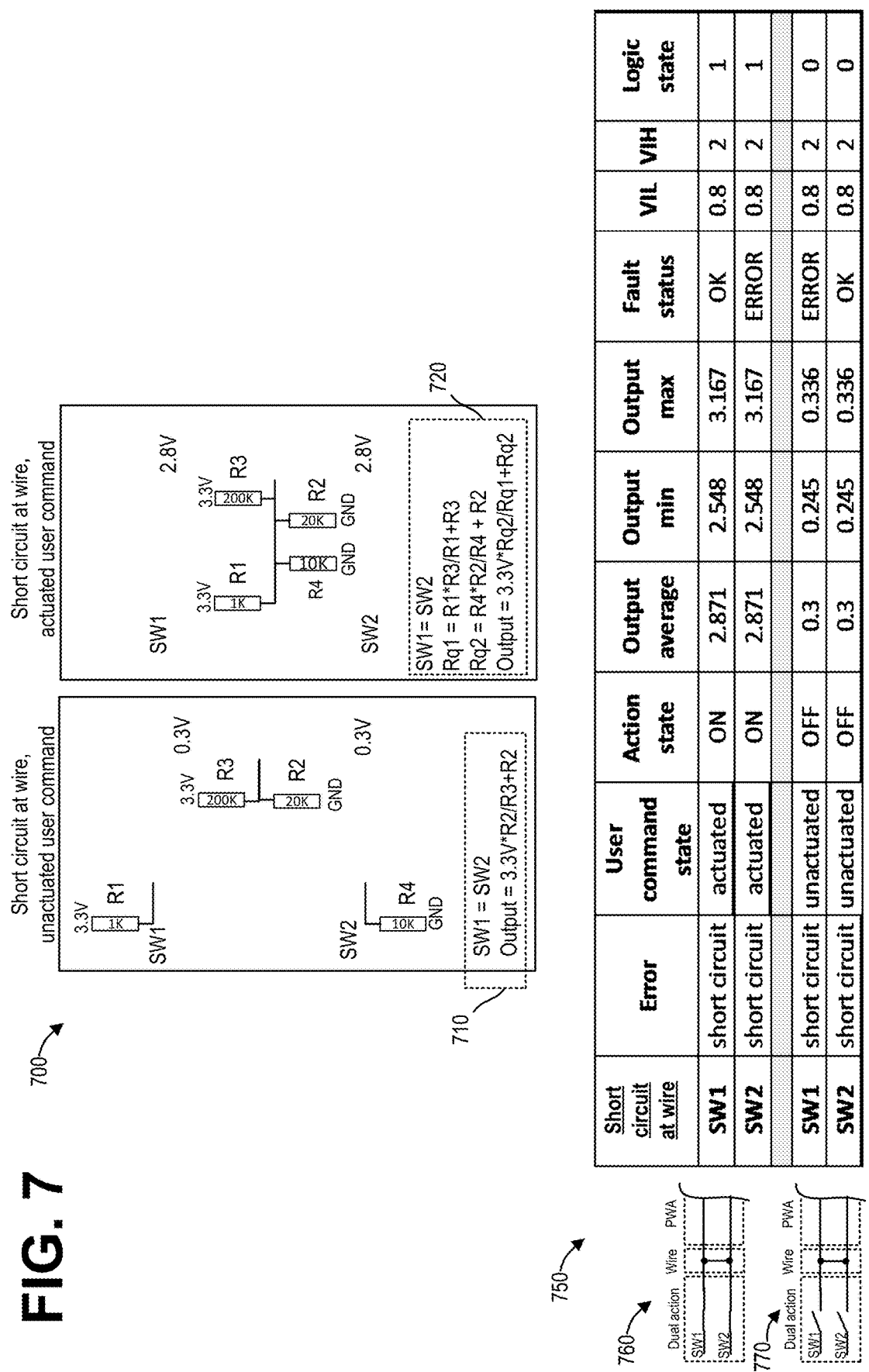

Turning now to FIG. 7, it shows a wire diagram 700 and corresponding data table 750 illustrating output signals and logic states arising from short circuits between the first dual actuator circuit and the second dual actuator circuit. As shown in wire diagram 700, for both the unactuated and actuated user command states, the output signals transmitted from both dual actuators is equal in the presence of a short circuit conductively coupling the dual actuator circuits (equations 710 and 720, respectively). Consequently, the logic states corresponding to each dual actuator are equal during an unactuated or actuated user command state, which generates a fault status for one of the dual switch actuators. For the case 760, where the user command state is actuated, the action states of each dual actuator is ON, but the logic state of SW2 (e.g., 1) is different from its normal logic state (e.g., 0) and an error fault status is indicated for SW2. Conversely, for the case 770, where the user command state is unactuated, the action states of each dual actuator is OFF, but the logic state of SW1 (e.g., 0) is different from its normal logic state (e.g., 1) and an error fault status is indicated for SW1.

As seen from FIG. 7, judicious selection of VIL, and VIH may also include selecting values of VIL and VIH to also account for a range of output signals arising from different error fault statuses. For the case of the short circuit between the first and second dual actuator circuits, VIH is selected (e.g., at 2.0V) so that the range of output signals arising from an ON action state is greater than VIH, thereby returning a logic state of 1 for both dual actuators. Similarly, VIL is selected (e.g., at 0.8V) so that the range of output signals arising from an OFF action state is less than VIL, thereby returning a logic state of 1 for both dual actuators.

Turning now to FIG. 8, it illustrates a data table 800 illustrating output signals and logic states arising from short circuits between the first dual actuator circuit to VCC (voltage common collector), and between the second dual actuator circuit to VCC. In one example, VCC may include the power source for each of the first dual actuator circuit and the second dual actuator circuit. As illustrated in cases 810, 820, 830, and 840, the short circuit to VCC (e.g., 3.3V) occurs between dual actuators SW1 and SW2 and the PWA 330. For cases 810 and 820, where a short circuit conductively couples the SW1 actuator circuit to VCC 3.3V, an output signal of 3.3 V is transmitted from the SW1 actuator to the PWA 330 during an unactuated and actuated user command state, respectively. During an unactuated user command state (e.g., case 810), the logic states output at the controller 1750 are equivalent (e.g., both logic states are 1); because the SW1 logic state is different from the SW1 normal logic state (0), an error fault status is indicated for SW1. During an actuated user command state (e.g., case 820), the logic states output at the controller 1750 for SW1 and SW2 are equivalent to the normal logic states for SW1 and SW2, respectively; as such, no error fault status is indicated for SW1 or SW2.

In contrast, for cases 830 and 840, where a short circuit conductively couples the SW2 actuator circuit to VCC 3.3V, an output signal of 3.3 V is transmitted from the SW2 actuator to the PWA 330 during an unactuated and actuated user command state, respectively. During an actuated user command state (e.g., case 840), the logic states output at the controller 1750 are equivalent (e.g., both logic states are 1); because the SW2 logic state is different from the SW2 normal logic state (0), an error fault status is indicated for SW2. During an unactuated user command state (e.g., case 830), the logic states output at the controller 1750 for SW1 and SW2 are equivalent to the normal logic states for SW1 and SW2, respectively; as such, no error fault status is indicated for SW1 or SW2.

Although not illustrated in FIG. 8, during conditions where short circuits conductively couple both SW1 and SW2 actuator circuits to VCC 3.3V, output signals of 3.3V are transmitted from both the SW1 and SW2 actuators to the PWA 330 during an unactuated and actuated user command state. As such, an equivalent logic state of 1 is generated for both dual actuators at the controller 1750, and an error fault status is indicated.

Figure 9:
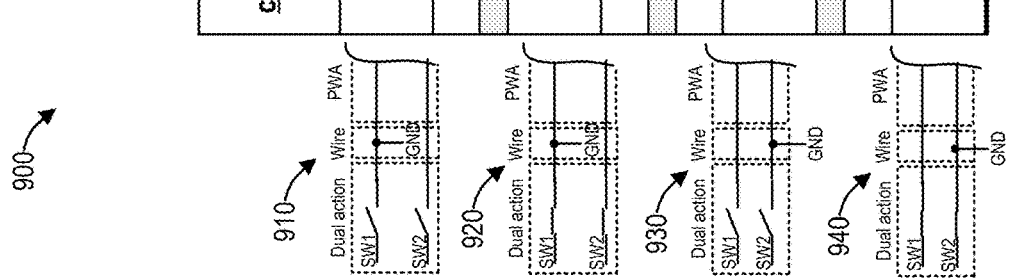
Figure 10:
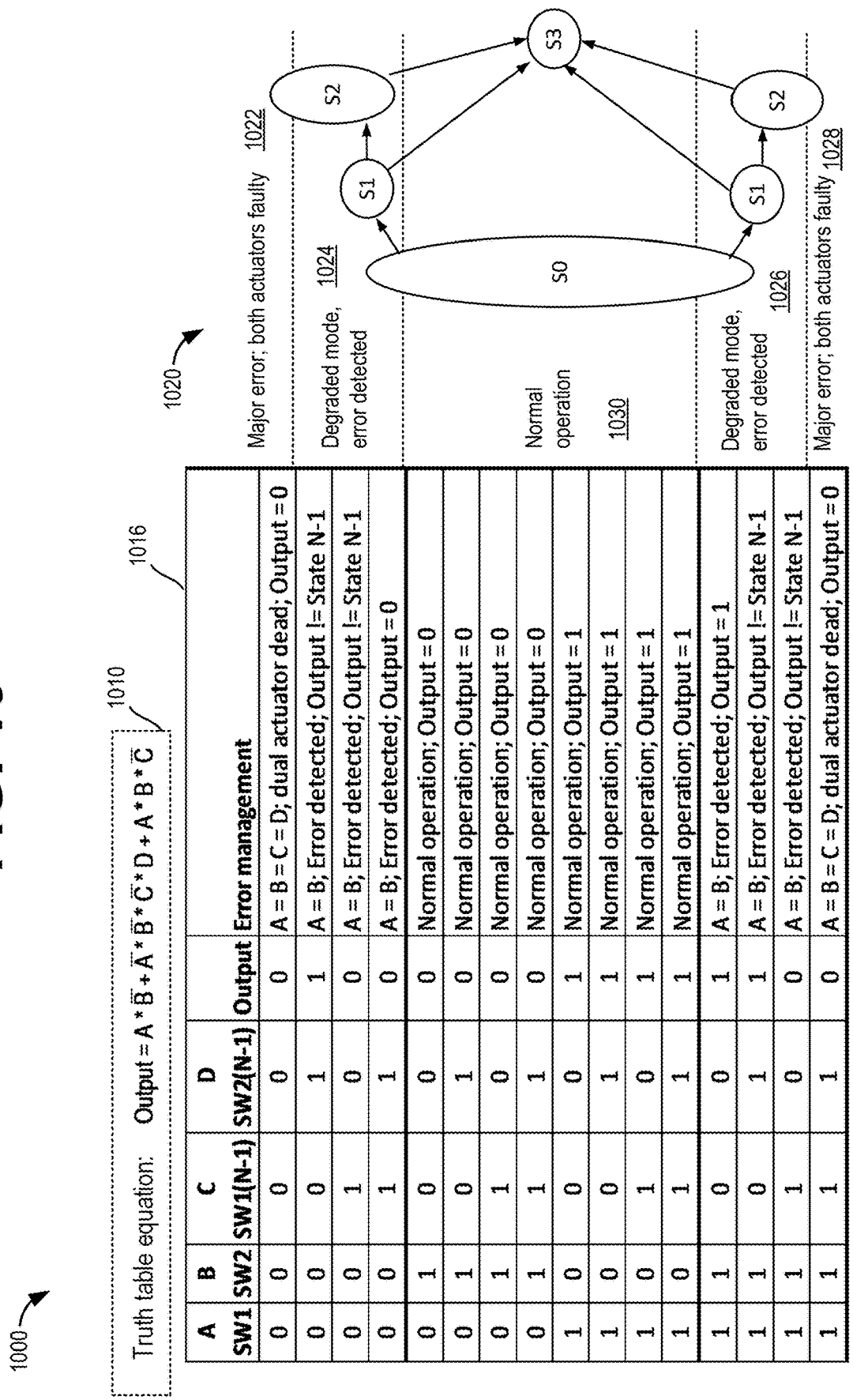
FIG. 10 shows a truth table for calculating truth table output logic states associated with a state machine of the electronic system of FIG. 3.

Turning now to FIG. 9, it shows a data table 900 illustrating output signals and logic states arising from short circuits between the first dual actuator circuit to ground (GND), and between the second dual actuator circuits to GND. As illustrated in cases 910, 920, 930, and 940, the short circuit to GND (e.g., 0V) occurs between dual actuators SW1 and SW2 and the PWA 330. For cases 910 and 920, where a short circuit conductively couples the SW1 actuator circuit to GND 0V, an output signal of 0 V is transmitted from the SW1 actuator to the PWA 330 during an unactuated and actuated user command state, respectively. During an unactuated user command state (e.g., case 820), the logic states output at the controller 1750 are equivalent (e.g., both logic states are 0); because the SW1 logic state is different from the SW1 normal logic state (1), an error fault status is indicated for SW1. During an unactuated user command state (e.g., case 910), the logic states output at the controller 1750 for SW1 and SW2 are equivalent to the normal logic states for SW1 and SW2, respectively; as such, no error fault status is indicated for SW1 or SW2.

In contrast, for cases 930 and 940, where a short circuit conductively couples the SW2 actuator circuit to GND 0V, an output signal of 0 V is transmitted from the SW2 actuator to the PWA 330 during an unactuated and actuated user command state, respectively. During an unactuated user command state (e.g., case 930), the logic states output at the controller 1750 are equivalent (e.g., both logic states are 0); because the SW2 logic state is different from the SW2 normal logic state (1), an error fault status is indicated for SW2. During an actuated user command state (e.g., case 940), the logic states output at the controller 1750 for SW1 and SW2 are equivalent to the normal logic states for SW1 and SW2, respectively; as such, no error fault status is indicated for SW1 or SW2.

Although not shown in FIG. 9, during conditions where short circuits conductively couple both SW1 and SW2 actuator circuits to GND 0V, output signals of 0V are transmitted from both the SW1 and SW2 actuators to the PWA 330 during an unactuated and actuated user command state. As such, an equivalent logic state of 0 is generated for both dual actuators at the controller 1750, and an error fault status is indicated. Furthermore, in some fields of application, the system and methods described herein may be programmed to provide fault tolerance analysis for multiple error types occurring simultaneously.

Turning now to FIG. 10, it illustrates a truth table 1000, including a representative truth table equation 1010 for calculating truth table output logic states for input to a state machine 1100 programmed at a PLD 1756 of the controller 1750. The state machine 1100 is partially represented by the state machine schematic 1020, which includes the relevant portions of state machine 1100 illustrating the states and state transitions therebetween corresponding to the truth table output logic states calculated by the truth table 1000.

As shown by truth table equation 1010, the truth table output logic state is calculated based on real-time logic states A and B of the first and second dual actuators SW1 and SW2, respectively; the historical logic states C and D of the first and second dual actuators SW1 and SW2, respectively; and the inverse logic states A, B, and C. For the truth table equation 1010, an output logic state of 0 corresponds to an unactuated user command state, whereas an output logic state of 1 corresponds to an actuated user command state. In the case of a continuously activated dual actuator motion control for a medical system, the unactuated user command state may correspond to when motion of the medical imaging system (e.g., gantry, lift, and/or patient table) is stopped; in contrast the actuated user command state may correspond to when motion of the medical imaging system (e.g., gantry, lift, and/or patient table) is started and active. Based on the real-time (A and B) and historical actuator states (C and D), the output logic states achieved in response to a sequence of user input commands, and state machine 1100, the methods and systems described herein may determine the presence of a fault in one or more of the actuators, and may further determine if the fault is due to a short circuit, open circuit, stuck actuator, and the like.

The real-time logic states refer to the current logic states; in other words, the dual actuator logic states calculated from the output signals most recently (e.g., most newly) transmitted to the controller 1750 from the dual actuators. In contrast, the historical logic states refer to the logic states calculated from the output signals more previously (e.g. less recently, less newly) transmitted to the controller 1750 from the dual actuators. Said another way, the historical logic states refer to the logic states calculated from output signals transmitted to the controller 1750 from the dual actuators prior to the output signals transmitted to the controller 1750 from the dual actuators from which the real-time logic states are calculated.

In the example of truth table 1000, the real-time logic states A and B refer to the $N^{th}$ logic states, and the historical logic states C and D refer to the $(N-1)^t$ logic states, wherein the $(N-1)^{th}$ logic state refers to the set of dual actuator historical logic states determined immediately previous to the set of dual actuator current real-time logic states. The executable instructions at the controller 1750 may include storing the dual actuator logic states as $(N-1)^{th}$ logic states C and D in memory thereat in response to an event that triggers the controller to determine the current logic states.

In one example a triggering event may include a change of state in the action state of one or both of the dual actuators, and subsequently receiving new output signals transmitted from the dual actuators; in response to receiving the new output signals, the controller may determine a new set of dual actuator real-time logic states from the newly transmitted output signals. A change of state in the action state of one or both of the dual actuators may be responsive to receiving a user command at the input device 1798 (e.g., pushing or releasing a button, changing a lever position, swiping a touch-sensitive interface, and the like). In another example, a change of state in the action state of one of the dual actuators may be responsive to a fault such as a stuck switch, short circuit, open circuit, and the like. In another example, a triggering event may include exceeding a threshold duration after the controller 1750 determining the most recent set of dual actuator logic states. The threshold duration may be selected to aid in ensuring that the controller 1750 updates the current logic states at a threshold frequency, even when a user command at an input device is maintained (e.g., no change in the dual actuator action state). Updating the current logic states at the threshold frequency may aid in increasing responsiveness in dual actuator fault detection, especially when continuous activation of the dual actuators is employed. In a further example, a triggering event may include when a rising signal edge or a falling signal edge in an output signal from one or both of the dual actuators is detected, indicating an imminent transition (or a transition that is underway) to a different action state in one or both of the dual actuators. In one embodiment, a rising and/or falling signal edge may be indicated by an absolute value of the first derivative of an actuator output signal being greater than a threshold first derivative; the threshold first derivative may be 0.

Furthermore, the controller 1750 may store a plurality of generations of historical logic states, whereby in response to receiving new output signals transmitted from the dual actuators and in response to determining a new (most recent) set of dual actuator real-time logic states from the most newly transmitted output signals, the controller 1750 may redesignate the $(N-1)^{th}$ set of dual actuator logic states as the $(N-2)^{th}$ set; the $N^{th}$ set of dual actuator logic states as the $(N-1)^{th}$ set; and the real-time logic states as the $N^{th}$ set of logic states. The truth table equation 1010 of FIG. 10 is an example embodiment. In other embodiments, additional historical logic states (e.g., one or more of $(N-1)^{th}$, $(N-2)^{th}$, $(N-3)^{th}$, ... $(N-M)^{th}$; where M is a whole number) may be included as inputs to a truth table equation for calculating the truth table output logic states. Said another way, one or more of the $(N-M)^{th}$ historical logic states may be included as inputs to determine the truth table output logic states and/or the state machine fault tolerance analysis.

Figure 11:
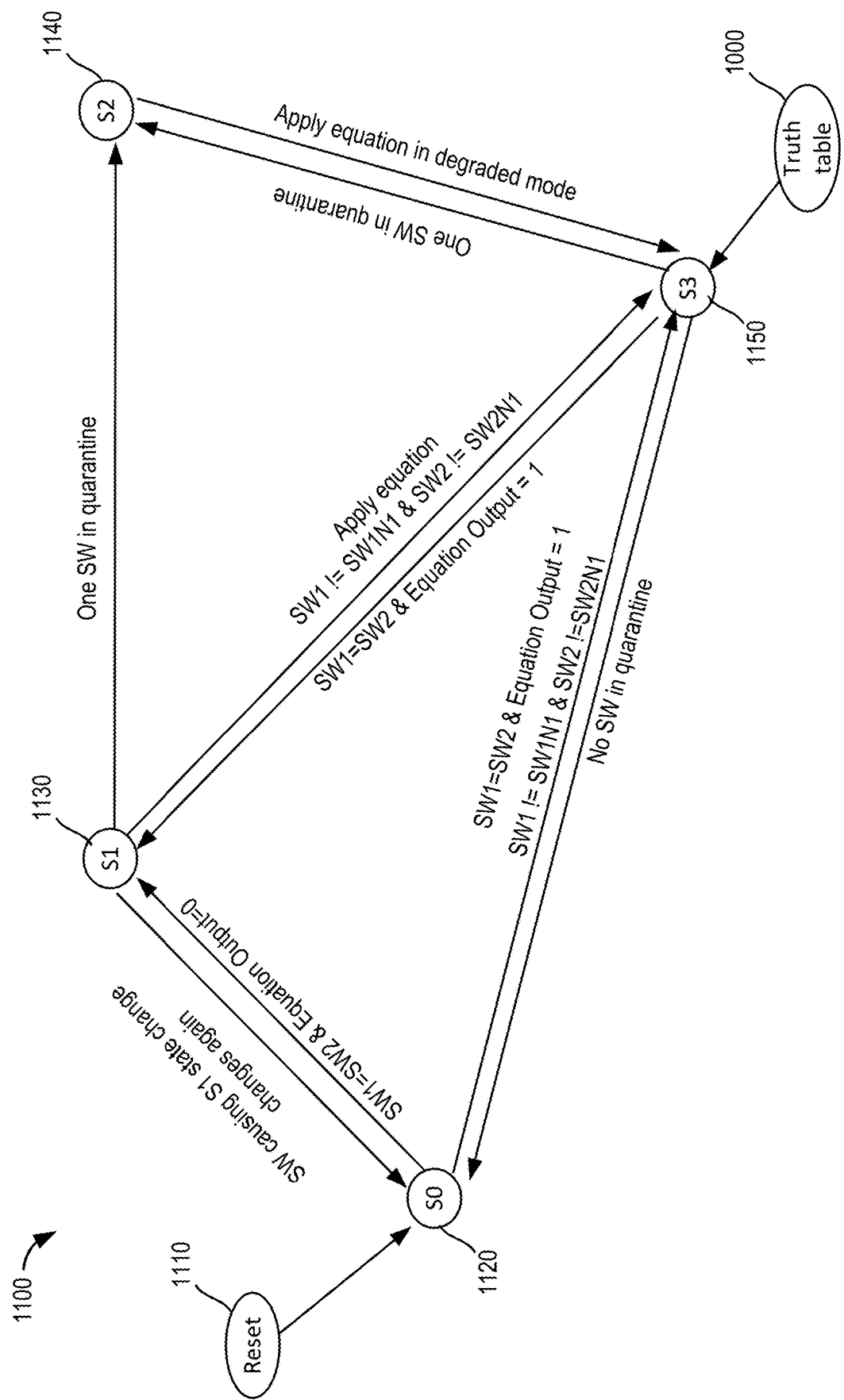
FIG. 11 shows an example state machine diagram for the electronic system of FIG. 3.

In the example of FIGS. 10-11, the truth table equation and state machine perform the fault tolerance analysis based on the current $(N^{th})$ and first generation historical $(N-1)^{th}$ (e.g., M=1) logic states. Referring back to data table 400, normal operation of the dual actuator is indicated when the logic state of the first dual actuator is different from (e.g., opposite to) the logic state of the second dual actuator. As described above with reference to FIGS. 5-9, the logic state of the first dual actuator being different from (e.g., opposite to) the logic state of the second dual actuator also corresponds to conditions when there is a fault with one or both of the dual actuators, but their action states are equivalent and consistent with the actuator action states during normal mode operation; in these cases, a user command can be executed and operation of the input device 1798 may be maintained normally in spite of the (non-detected) actuator fault. Thus, in response to a condition including when the current logic state of SW1 is not equivalent to current the logic state of SW2, the operational status of the dual actuated input device 1798 may be determined to be normal mode condition (e.g., indicating absence of a detectable error fault status) by the fault tolerance analysis, as indicated by region 1030 and methods described herein. Furthermore, even in cases where one or more sets of historical (e.g., $(N-1)^{th}$ logic states) actuator logic states are equivalent (e.g. SW1 (N-1)=SW2 (N-1), indicating the presence of a previous actuator error fault status, because the current real-time actuator logic states are different, the previous actuator fault is presumed to have cleared, and normal mode operation is indicated at the controller 1750.

As shown in FIG. 10, the region of normal operation 1030 corresponds to the states S0 and S3 of the state machine 1100. As further described with reference to FIG. 11, state S0 may also be reached during a condition including while waiting for a triggering event, including receiving additional user input 1722 at the input device 1798 responsive to a change in the user command state, a change in the action state of an actuator, and exceeding a threshold duration since the last user input 1722 was received at the input device 1798. In contrast, the state S3 is reached during a condition including when the error fault status (e.g., normal, faulty) is known and stable, and the truth table equation is to be applied. In one example, the state machine may transition from the state S0 to the state S3 in response to a triggering event.

The regions 1022 and 1028 correspond to a condition when both sets of current real-time (e.g. $N^{th}$) and historical (e.g. $(N-1)^{th}$) actuator logic states are equivalent to each other (e.g., SW1=SW2=SW1 (N-1)=SW2 (N-1)). Because the current dual actuator states and their corresponding historical actuator states are all equivalent (e.g., SW1=SW1 (N-1) and SW2=SW2 (N-1)), a error fault status in both of the dual actuators and a major fault is indicated because the logic states have been unresponsive (e.g., have not responsively changed state) to triggering events such as a change in user input 1722 at the input device 1798, exceeding the threshold duration, and a change in the action state. During conditions when both dual actuators are faulty, the dual actuated input device 1798 becomes inoperable, and the controller 1750 may responsively transmit a message to the user via a display console indicating a major error and to repair the input device 1798. As indicated in FIG. 10, regions 1022 and 1028 may correspond to the state S2 of the state machine 1100; however, detection and reporting of a dead switch may be executed in each state of the state machine 1100.

The regions 1024 and 1026 correspond to when the current logic states of the dual actuators are equivalent, and at least one of the dual actuator logic states has changed state from its previous historical (e.g., $(N-1)^{th}$) logic state. Furthermore, regions 1024 and 1026 may correspond to when the output of the truth table equation is different from one or more of historical logic states C and D. As such, an error mode is indicated in response to detection of an error fault status at one of the dual actuators and the controller 1750. As further described with reference to FIG. 11-16, when entering error mode, the state machine transitions from state S0 to state S1 and/or S2, to assess and determine the type of actuator fault (e.g., short circuit, open circuit, stuck actuator, and the like), and whether the operation of the dual actuator and execution of the user command may be maintained in the presence of the actuator fault. This determination by the state machine 1100 may be based on the truth table output logic state, the current logic states A and B, and the historical logic states C and D. If the error fault status persists beyond a threshold delay, the operational status of the input device 1798 may progress to degraded mode. If only one of the dual actuators is degraded, operation of the dual actuated input device 1798 may be maintained by the controller. In this way, the robustness and fault tolerance of the electronic system can be increased relative to conventional dual actuated systems.

Turning now to FIG. 11, it illustrates a state machine diagram 1100 for determining operation of the dual actuated input device 1798 in the presence of an error fault status in at least one of the dual actuators. As described herein, the state machine may be programmed at a programmable logic device 1756 such as FPGA 338, as part of executable instructions residing at a controller 1750 of the electronic system. The state machine diagram 1100 includes four nodes representing four states: S0 1120, S1 1130, S2 1140, and S3 1150; the arrows connecting two different nodes represent transitions from one of the four states to another of the four states. At each of the four states, the controller 1750 waits until a condition is met or an event is received before executing a transition to a different state. Each transition arrow is labeled with the input or condition (e.g., event) that triggers the corresponding transition. Each of the transitions to a different state can include a set of executable actions or instructions, and may include entry actions, which are performed when entering a state, and exit actions, which are performed when exiting a state.

In addition to the four states, the state machine diagram 1100 also shows reset 1110, and truth table 1000. As described above with reference to FIG. 10, during the state S3 1150, the controller 1750 may calculate the logical output value from the truth table 1000 to aid in evaluating the current error fault status. Reset 1110 may refer to initialization conditions prior to entering S0. For example, upon initial supply of power ON to the dual actuated input device 1798, or following repair or maintenance to correct a persistent fault in the dual actuated input device 1798. State S0 indicates that the dual actuated input device 1798 in operating in a normal mode state, without error fault status at either dual actuator. During a condition corresponding to state S0, dual actuator operating conditions are monitored and state transitions to S1 and/or S3 may be executed based on changes to dual actuator logic states, action states, and/or triggering events.

The state machine nodes and transitions are represented in method flow charts 1300, 1400, 1500, and 1600 of FIGS. 13-16, respectively. Similar to the method 1200, methods 1300, 1400, 1500, and 1600 may include executable instructions residing at the controller 1750 for operating an electronic system including a dual actuated input device 1798. Furthermore, method 1200 includes executable instructions corresponding to performing a state machine analysis to determine the fault status of the dual actuated input device 1798, as represented by the flow charts of FIGS. 13-16, respectively.

Figure 12:
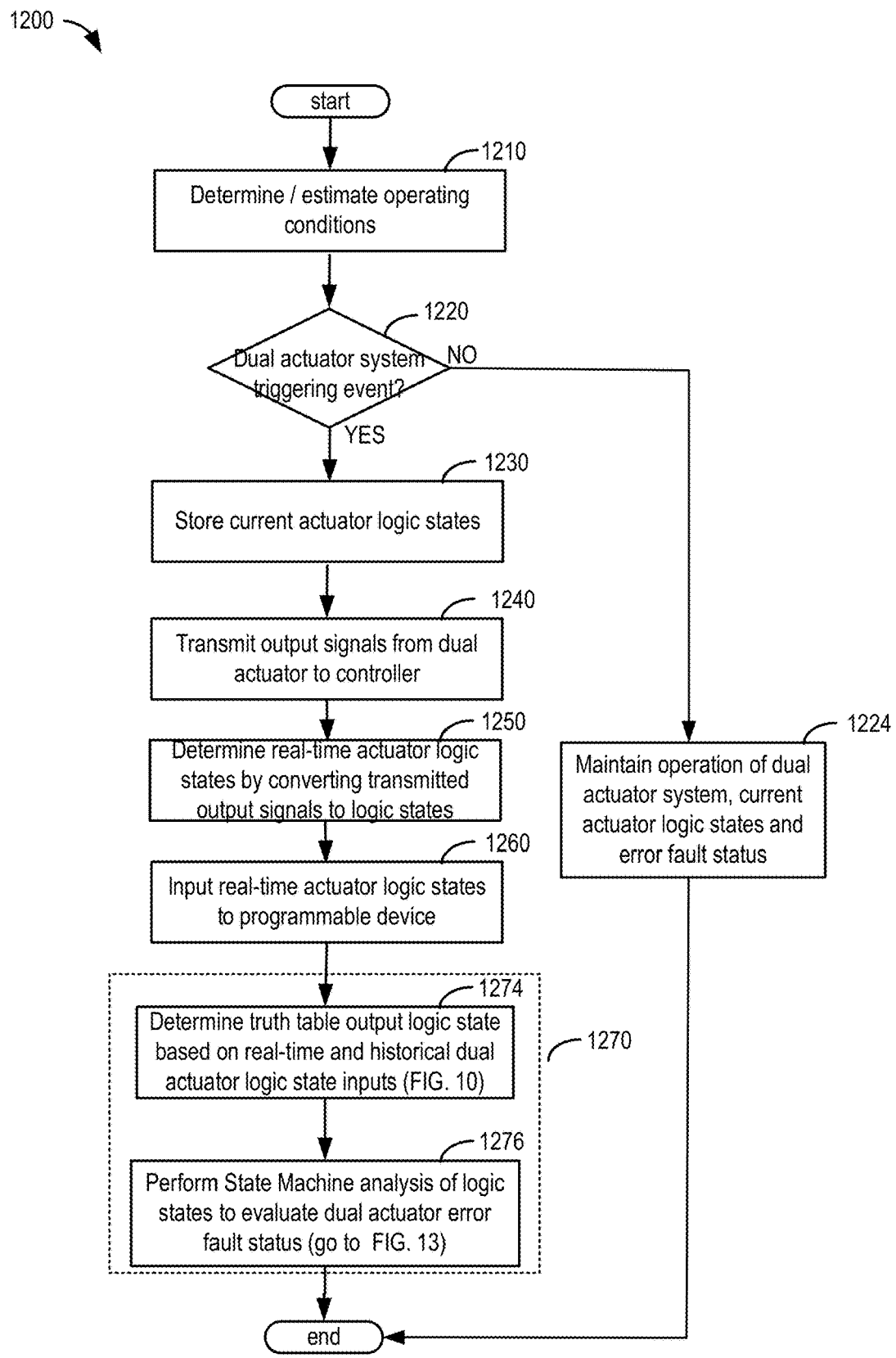
FIGS. 12-16 show flow charts for example methods of operating the electronic system of FIG. 3.

Turning now to FIG. 12, method 1200 begins at 1210, where various operating conditions of the electronic system and dual actuated input device 1798 are estimated and/or determined. Example conditions may include a power status (e.g., ON/OFF) supplied to the dual actuated input device 1798, and the like. In the case of a medical imaging system 100, determining operating conditions at 1210 may include determining if a patient's body 190 is present at the patient table 194, if an alignment of a radiation detector 108 and a radiation source 106 are aligned and ready, if power is supplied to one or more operator console display monitors 128 and 138, and the like. In some examples, determining the operating conditions at 1210 may include initialization of the dual actuated input device 1798, such as when power is first supplied thereat. As such, initialization may include determining the initial status of each of the dual actuators by measuring the output signals transmitted therefrom and determining the corresponding real-time logic states. During initialization, the output signals and logic states of each of the dual actuators may correspond to their default output signals and logic states in an unactuated action state.

Method 1200 continues at 1220 where the controller 1750 determines if a triggering event is detected. As described above, a triggering event of the dual actuated input device 1798 may include one or more of a change in user input 1722 at the input device 1798, exceeding the threshold duration since last receiving user input 1722 at the input device 1798, and a change in the action state of one of the dual actuators. In the case where no triggering event is detected, method 1200 continues at 1224 where the controller 1750 maintains operation of the dual actuated input device 1798. In the absence of any new user input 1722 at the input device 1798 or any change in the actuator action states, the current dual actuator output signals and logic states are maintained. After 1224, method 1200 ends.

Responsive to the condition including where a triggering event is detected, method 1200 continues at 1230 where the controller 1750 stores the current dual actuator logic states in non-transitory memory at the controller 1750. In particular, the current (e.g., $N^{th}$) actuator logic states are stored as the $(N-1)^{th}$ historical logic states; and any preceding $(N-M)^{th}$ logic state stored in memory may be shifted and redesignated in memory to the $(N-M-1)^{th}$ logic state. In this way, the controller 1750, responsive to the triggering event at 1220, can accommodate a new set of real-time dual actuator logic states. The new actuator logic states are determined at 1250 by converting the real-time output signals received from the dual actuators at comparators 1754. In the example of FIG. 3, the comparators 1754 may include an inverter with a Schmitt trigger. As described herein with reference to FIG. 3, the dual actuator logic states may be determined by comparing the output signal values to a lower threshold signal, VIL, and an upper threshold signal, VIH. During a condition when an actuator output signal is less than VIL, a first logic state is determined; during a condition when the actuator output signal is greater than VIH, a second logic state, opposite from the first logic state is determined. In the example of FIG. 3, the first logic state is 0 and the second logic state is 1.

Next, at 1260, the real-time logic states are input by the controller 1750 to the PLD 1756. In the example of FIG. 3, PLD 1756 may include the FPGA 338. Subsequently, method 1200 continues at 1270 where the controller 1750 performs fault tolerance analysis of the dual actuated input device 1798. At 1274, the controller 1750 may execute instructions stored thereon to determine a truth table output logic state based on the real-time and historic dual actuator logic states input to the PLD 1756, as described with reference to FIG. 10. Next, at 1276, the fault tolerance analysis utilizes the state machine 1100 based on the calculated truth table output logic state, along with the real-time and historical logic states to perform a fault tolerance analysis to determine the error fault statuses of each of the dual actuators. As described below with reference to FIGS. 11-15, in response to a condition including when both dual actuators have faulty error statuses, the controller may stop operation of the dual actuator system and reports a major error to the operator; in response to one of the dual actuators having a faulty error status, the controller may indicate a degraded actuator and maintain operation of the dual actuator system; in response to none of the dual actuators having a faulty error status, the controller may maintain operation of the dual actuator system.

Figure 13:
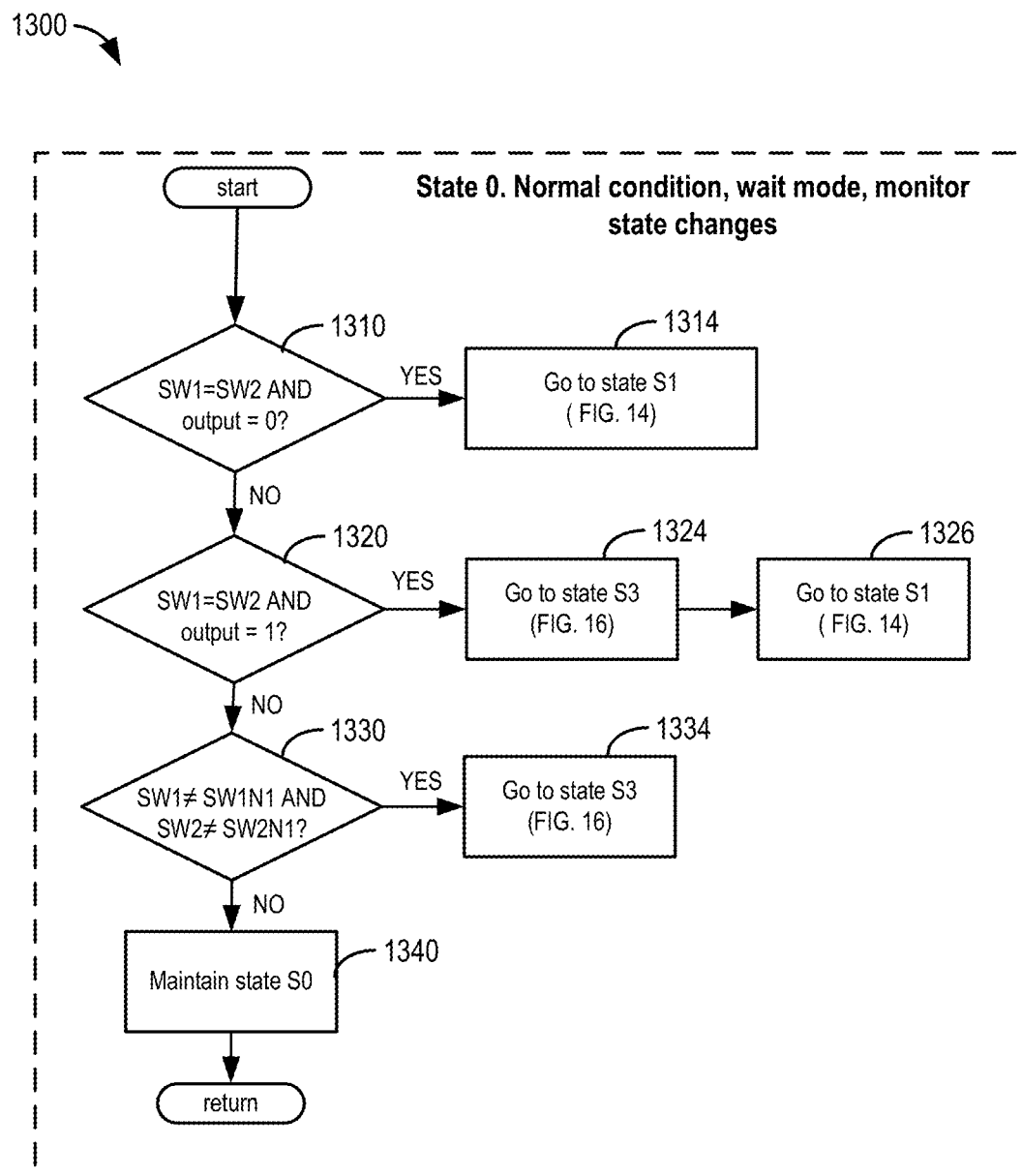

Referencing FIG. 10 and FIGS. 13-16, the state machine analysis begins at state S0 corresponding to normal mode operating condition (FIG. 13, method 1300). During the state S0, the controller 1750 may determine a state transition to state S1 or state S3, depending on the nature of the dual actuator logic state transitions; in particular, the controller may execute method 1300 at 1310 to determine if SW1=SW2 AND output=0. Here, SW1 refers to the real-time logic state of SW1 (e.g., A in table 1000), SW2 refers to the real-time logic state of SW2 (e.g., B in Table 1000), and output refers to the calculated output logic state value from the truth table equation 1010. As an example, referring to the data table 900 and the truth table 1000, transitioning from an actuated state ((N−1)$^{th}$ state) to an unactuated state in the presence of a short circuit to GND at SW2 satisfies the condition SW1=SW2 AND output=0. Similarly, referring to data table 800 and truth table 1000, transitioning from an actuated state ((N−1)$^{th}$ state) to an unactuated state in the presence of a short circuit to VCC at SW1 satisfies the condition SW1=SW2 AND output=0. As other examples, referring to data table 500, and truth table 1000, the scenarios of transitioning from an actuated to an unactuated state in the presence of SW2 stuck CLOSED; transitioning from an actuated to an unactuated state in the presence of SW1 stuck CLOSED satisfy the condition SW1=SW2 AND output=0. In the case where the condition SW1=SW2 AND output=0 is satisfied (corresponding to an unactuated user command state), method 1300 continues at 1314, transitioning to state S1.

Figure 14:
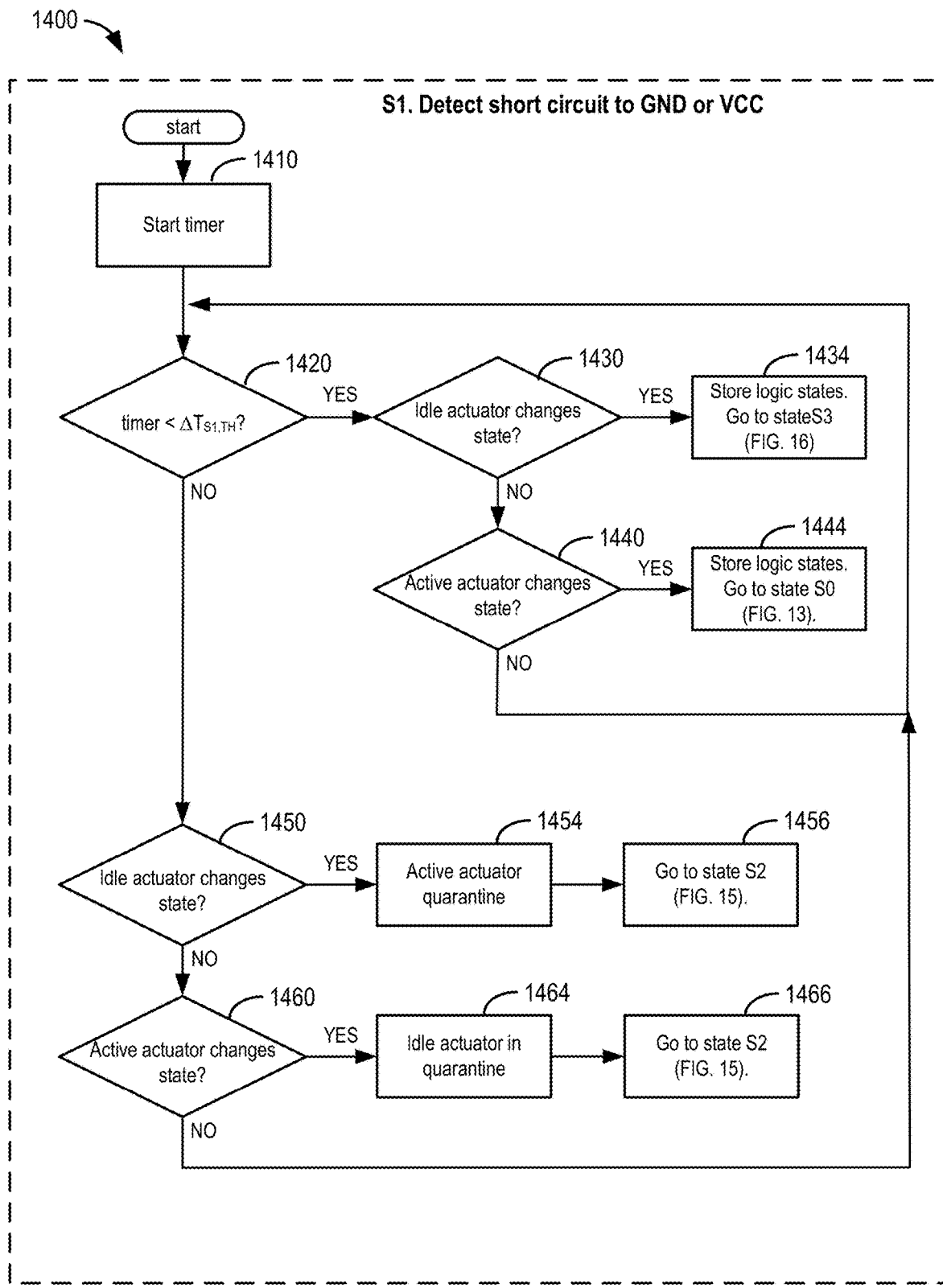

The method continues at 1410 of FIG. 14, as part of state S1, to analyze the dual actuator logic state transition by determining if a fault is indicated at one of the dual actuators. As further described herein, by monitoring the sequence of transitions in logic states of each of the dual actuators responsive to one or more user input(s) 1722 received at the dual actuated system, the system and methods described herein may discern the nature or cause of an actuator fault (e.g., short circuit, open circuit, stuck actuator, and the like) by following the steps and logic of the state machine 1100 and referencing the data tables in FIGS. 4 through 10. In particular, and as further described herein, while in state S1, the nature of the actuator fault may be determined by monitoring the transitions of the dual actuators (e.g., the active and idle actuators, as described below) in response to a sequence of user inputs 1722. Depending on the transitions and/or idleness of each of the dual actuators responsive to the sequence of user inputs 1722, a fault may be attributed to a short circuit, open circuit, stuck actuator, and the like; furthermore, the systems and methods herein can discern, based on the transitions and/or idleness of each of the dual actuators responsive to the sequence of user inputs 1722, if the fault is originating from actuator SW1 or SW2.

For example, in response to a (non-normal mode) condition when SW1=SW2 (e.g., A=B), the method waits for a subsequent dual actuator state transition and determines if the non-normal mode condition arose from a user input command action or from a short circuit to GND or VCC. In this way, the method may perform a fault analysis, including differentiating between a short circuit fault type and other fault types such as stuck actuator or open circuit. Further details are described herein with reference to FIGS. 10-16.

For the case where the condition at 1310 is not satisfied, method 1300 continues at 1320 where the controller 1750 determines if the condition SW1=SW2 AND output=1 is satisfied. As examples, referring to data tables 500, 600, 800, 900, and truth table 1000, the scenarios of: transitioning from an actuated state to an unactuated state in the presence of SW1 stuck OPEN; transitioning from an actuated state to an unactuated state in the presence of SW2 stuck OPEN; transitioning from an unactuated state to an actuated state in the presence of an open circuit at SW1 or SW2; transitioning from an unactuated state to an actuated state in the presence of a short circuit to VCC at SW2; and transitioning from an unactuated state to an actuated state in the presence of a short circuit at GND, each satisfy the condition SW1=SW2 AND output=1. In the case where the condition SW1=SW2 AND output=1 is satisfied, method 1300 continues at 1324, transitioning to state S3.

The method continues at 1610 of method 1600 where the controller applies the truth table equation 1010, considering whether to halt the actuated user command state, even in the presence of an actuator fault such as a short circuit. As described previously with reference to FIG. 11, the truth table output logic state of 1 corresponds to an actuated user command state; as such, applying the truth table equation 1010 during state S3 allows for an opportunity to stop the actuated user command state, prior to performing the fault analysis at state S1 at 1326. For example, stopping the actuated user command state may correspond to the case where applying the truth table equation 1010 during state S3 yields a truth table output logic state of 0, where the user command state has been driven to 0 and unactuated. In the case of a medical imaging system, actuated motion of the imaging system may be stopped, thereby driving the output logic state of the truth table equation 1010 to 0 during state S3, when the truth table equation 1010 is applied. In contrast, the condition SW1=SW2 AND output=0 at 1310 corresponds to an unactuated user command state; as such the controller may proceed from state S0 at 1310 to state S1 to analyze the actuator fault, bypassing state S3. After 1324, method 1300 continues at 1326, transitioning to state S1. The method continues at 1410 of FIG. 14 to determine if a short circuit fault is indicated at one of the dual actuators.

For the case where the condition at 1320 is not satisfied, method 1300 continues at 1330 where the controller 1750 determines if the condition SW1≠SW1N1 AND SW2≠SW2N1 is satisfied. As an example, referring to FIG. 7, transitioning from an actuated to an unactuated user command state during a condition including when a short circuit between the first actuator circuit and the second actuator circuit is present satisfies the condition SW1≠SW1N1 AND SW2≠SW2N1. In contrast, referencing FIGS. 8 and 9, there are no conditions corresponding to a short circuit to GND or VCC, open circuit, or stuck OPEN/

CLOSED actuator for the dual actuated input device 1798 that satisfy the condition SW1≠SW1N1 AND SW2≠SW2N1. As such, satisfying the condition SW1≠SW1N1 AND SW2≠SW2N1 may indicate a short circuit between the first and second actuator circuits. For the case where the condition SW1≠SW1N1 AND SW2≠SW2N1 is satisfied, method 1300 continues at 1334, transitioning to state S3. The method continues at 1610 of FIG. 16 to apply the truth table equation.

In a rare case of different types of fault errors occurring concurrently at both dual actuators such as a short circuit to GND at SW2 ((N−1)$^{th}$ state) followed by a short circuit to VCC at SW1 (N$^{th}$ state) satisfying the condition SW1≠SW1N1 AND SW2≠SW2N1 at 1330, the method continues by way of the controller executing step 1334 to proceed to state S3, reapplying the truth table equation 1010. If both faults persist, the controller returns state S0, where either condition at 1310 or 1320 is satisfied; next, following the methods described herein with reference to FIGS. 12-16, state transitions to state S1 (where the system may differentiate the fault error types at both dual actuators) and state S2 may lead to detection of faulty error states in both dual actuators at 1530, and stopping operation of the dual actuator system at 1534.

For the case where the condition at 1330 is not satisfied, the state S0 is maintained at 1340, indicating that the dual actuated input device 1798 is operating normally. After 1340, method 1300 returns to method 1200 after 1276, where method 1200 ends.

Turning to FIG. 14, it illustrates a method 1400 including executable instructions corresponding to the state S1 of the state machine 1100. During the state S1, the controller 1750 may detect if the error fault status in one of the dual actuators is caused by a short cut to VCC or GND by monitoring the dual actuators for subsequent changes to their logic states. The state S1 is reached when the operational state of the dual actuated input device 1798 changes from a normal mode condition when SW1≠SW2 to an error condition when SW1=SW2 because one of the dual actuators (e.g., one of SW1 and SW2) has undergone a change in its logic state. That particular actuator, having undergone a change in its logic state, thereby newly satisfying the condition SW1=SW2, may be referred to as the active actuator during the state S1, whereby the historical (N−1)$^{th}$ logic state of the actuator is inequivalent to its current real-time N$^{th}$ state. In contrast, the other actuator, having maintained a constant logic state, may be referred to as the idle actuator during the state S1, whereby the historical (N−1)th logic state of the idle actuator is equivalent to its current real-time N$^{th}$ logic state.

Method 1400 begins at 1410 where the controller 1750 initializes and starts a timer. The duration indicated by the timer represents a measure of the time elapsed since the SW1=SW2 condition was detected. Next, method 1400 continues at 1420 where the controller 1750 determines if the time elapsed as indicated by the timer is less than a threshold S1 duration, $\Delta T_{S1,TH}$. $\Delta T_{S1,TH}$ may correspond to a delay time or duration before which one or both of the dual actuators may be transitioning to a different logic state in response to a user input command. As described herein, the dual actuators may be concurrently actuated in response to a user input command 1722 at the input device 1798; however, concurrent actuation may include actuating the first actuator and then actuating the second actuator only after a threshold delay has elapsed. As such, $\Delta T_{S1,TH}$ may include a duration of the threshold delay; in one example, $\Delta T_{S1,TH}$ may include 1.5 s. In other examples, $\Delta T_{S1,TH}$ may correspond to a desired threshold delay for a dual actuated input device 1798 operating in a particular application or environment of the electronic system 1700. In particular, the value of the threshold delay may be selected to allow for the dual actuators (under normal non-faulty conditions) to (e.g., complete the) transition to their new logic states responsive to a received user input 1722. As such, the value of the threshold delay may vary depending on the particular type of dual actuator technology, and depending on the application and/or environment in which the dual actuator system is utilized.

Prior to $\Delta T_{S1,TH}$ elapsing, one of the dual actuators may be in a transitory condition, having not yet completed the migration to a new logic state. Thus, when timer $\ll\Delta T_{S1,TH}$, the SW1=SW2 condition may be satisfied because one or both of the actuators are in a transitory condition. For the case where timer $<\Delta T_{S1,TH}$, method 1400 proceeds to 1430 where it determines if the logic state of the idle actuator has changed. If the idle actuator changes logic state when timer $<\Delta T_{S1,TH}$, the condition SW1=SW2 is no longer satisfied, and method 1400 continues to 1434, where the controller 1750 stores the dual actuator logic states before triggering a state transition from state S1 to state S3 to calculate a new truth table equation output value. The idle actuator changing logic state prior to $\Delta T_{S1,TH}$ indicates that the dual actuated input device 1798 may not have an error fault status, since the SW1=SW2 condition was satisfied only for a duration less than $\Delta T_{S1,TH}$. Furthermore, storing the logic states at 1434 may include storing the current dual actuator logic states in non-transitory memory at the controller 1750. In particular, the current (e.g., N$^{th}$) actuator logic states are stored as the (N−1)$^{t}$ historical logic states; and any preceding (N−M)$^{th}$ logic state stored in memory may be shifted and redesignated in memory to the (N−M−1)$^{th}$ logic state.

Returning to 1430, for the case where the idle actuator has not changed logic state, method 1400 continues at 1440 where the controller 1750 determines if the active actuator has undergone a change in logic state. In response to the active actuator changing state, the condition SW1=SW2 is no longer satisfied, and method 1400 continues at 1444 where the controller 1750 stores the dual actuator logic states prior to triggering a state transition from state S1 to state S0. Said another way, if the active actuator changes logic state prior to $\Delta T_{S1,TH}$, a "false positive" transient error fault status is indicated, and normal mode operation is maintained by the controller 1750. In this way, a risk of interrupting execution of user commands and operation of the electronic system 1700 responsively to momentary error fault statuses, indicated by a condition being met when SW1=SW2 AND timer$<\Delta T_{S1,TH}$, may be averted, thereby increasing a robustness of the dual actuated input device 1798. Furthermore, storing the logic states at 1444 may include storing the current dual actuator logic states in non-transitory memory at the controller 1750. In particular, the current (e.g., N$^{th}$) actuator logic states are stored as the (N−1)$^{th}$ historical logic states; and any preceding (N−M)$^{th}$ logic state stored in memory may be shifted and redesignated in memory to the (N−M−1)$^{th}$ logic state. Returning to 1440, in the case where the active actuator does not change state, method 1400 returns to 1420.

Returning to 1420, for the case where timer is not less than $\Delta T_{S1,TH}$, method 1400 continues to 1450 where the controller 1750 determines if the idle actuator has changed logic state. In the case where the idle actuator has changed logic state after a duration greater than $\Delta T_{S1,TH}$ has elapsed, method 1400 continues at 1454, where the controller 1750 indicates that the active actuator is in quarantine status (e.g., the actuator is associated with an error fault status). Because the elapsed time>$\Delta T_{S1,TH}$, the change in the logic state of the idle actuator may occur responsively due to a user command 722 at input device 1798; for example, a user may release a motion control button for continuously activating a motion control system in an x-ray imaging system. Thus, the idle actuator is functioning normally, and the active actuator may be faulty. Method 1400 continues at 1456, where the controller 1756, in response to placing the active actuator in quarantine status, triggers a state transition from state S1 to state S2.

Returning to 1450, for the case where a change in logic state of the idle actuator when timer<$\Delta T_{S1,TH}$ is not detected, method 1400 continues to 1460 where the controller 1750 determines if the active actuator has changed logic state. In the case where the active actuator has changed logic state after a duration greater than $\Delta T_{S1,TH}$ has elapsed, method 1400 continues at 1464, where the controller 1750 indicates that the idle actuator is in quarantine status. Because the elapsed time>$\Delta T_{S1,TH}$, the change in the logic state of the active actuator may occur responsively due to a user command 722 at input device 1798; for example, a user may release a motion control button for continuously activating a motion control system in an x-ray imaging system. Thus, the active actuator is functioning normally, and the idle actuator may be faulty. Method 1400 continues at 1466, where the controller 1756, in response to placing the idle actuator in quarantine status, triggers a state transition from state S1 to state S2. Returning to 1460 for the case where a change in logic state of the active actuator when timer <$\Delta T_{S1,TH}$ is not detected, method 1400 returns to 1420.

Figure 15:
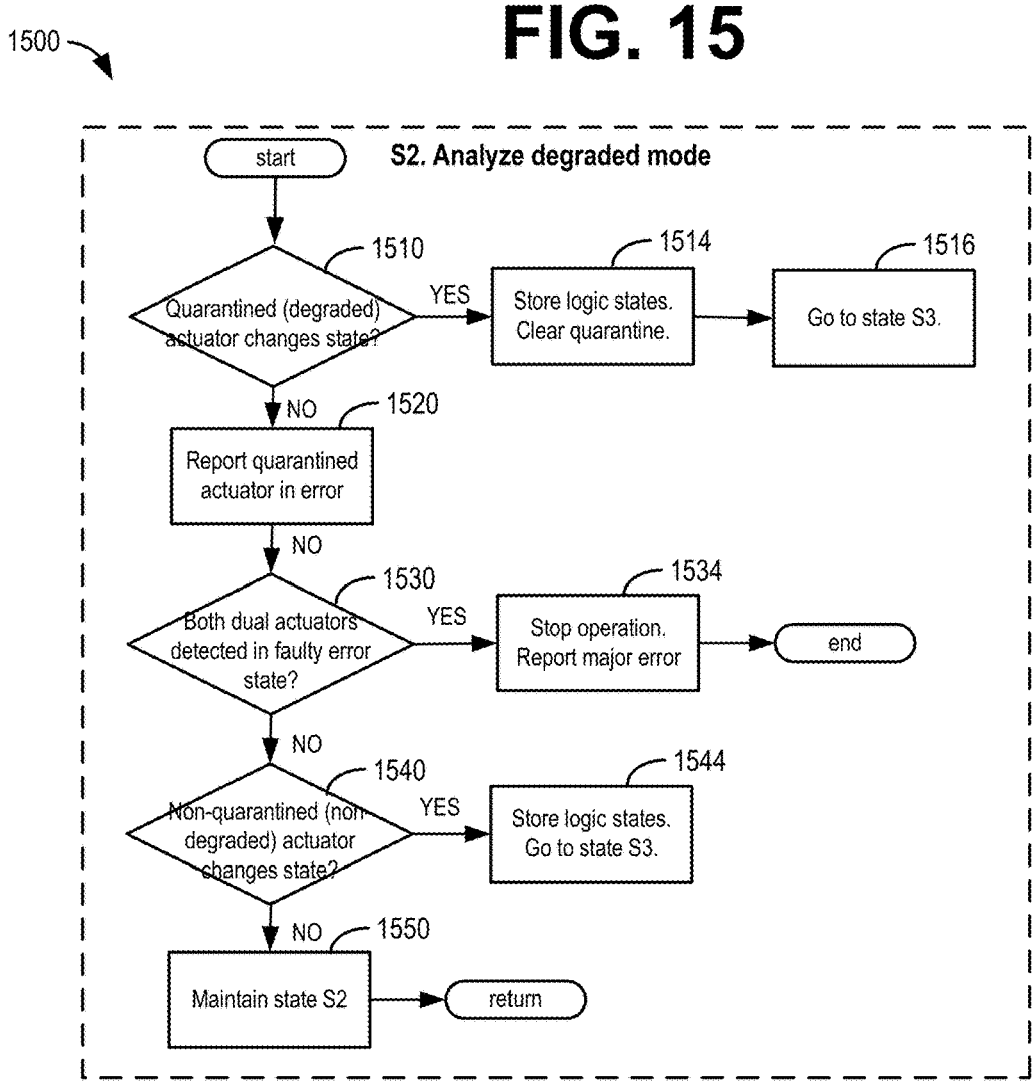

Turning now to FIG. 15, it illustrates a method 1500 including executable instructions corresponding to the state S2 of the state machine 1100. The state S2 corresponds to a degraded mode, and is reached during a condition responsive to at least one of the dual actuators being placed in quarantine status. As described herein, operation of the dual actuator system may be maintained responsive to an error fault status (including a quarantine status) indicated at only one of the dual actuators. During the state S2, the controller 1750 may monitor the quarantined actuator for subsequent changes in logic state, which may aid in indicating sustained error fault statuses. Method 1500 begins at 1510, where the controller 1750 determines if a quarantined actuator changes logic state. Determining if the quarantined actuator changes logic state at 1510 may be responsive to a triggering event, including one or more of a change in a user command state, a change in the actuator action state, and exceeding a threshold duration, as described above. A change in the logic state of the quarantined actuator may indicate that the actuator function has returned or resumed. Thus, responsive to a change in the logic state of the quarantined actuator, method 1500 continues at 1514, where the controller 1750 stores the dual actuator logic states prior to clearing the quarantine status for that actuator. Furthermore, storing the logic states at 1514 may include storing the current dual actuator logic states in non-transitory memory at the controller 1750. In particular, the current (e.g., $N^{th}$) actuator logic states are stored as the $(N-1)^{th}$ historical logic states; and any preceding $(N-M)^{th}$ logic state stored in memory may be shifted and redesignated in memory to the $(N-M-1)^{th}$ logic state. After 1514, method 1500 continues at 1516, where the controller 1750 triggers a state transition from the state S2 to the state S3, in order to reassess the status of the dual actuated input device 1798 including recalculating the truth table equation output.

Returning to 1510, for the case where the quarantined actuator does not change state, including in response to a triggering event, method 1500 continues at 1520 where the quarantined actuator is reported to be in error (fault status). Although one of the two dual actuators may be in error fault status, operation of the electronic system and execution of the user command at input device 1798 may be sustained by the controller 1750. Alternately, upon receiving the report of the quarantined actuator, the user may optionally stop operation of the electronic system in order to examine and/or rectify the error fault. In this way, fault tolerance of the dual actuated input device 1798 may be increased, while maintaining adherence to industry standards.

Next, method 1500 continues at 1530 where the controller 1750 determines if both dual actuators are detected in faulty state corresponding to when A=B=C=D AND the truth table output=0 (see truth table 1010). When both dual actuators are in faulty state, the dual actuated input device 1798 is inoperable. Thus, responsive to both dual actuators being in a faulty state, method 1500 continues at 1534 where a major error is reported and operation of the dual actuated input device 1798 is stopped. After 1534, method 1500 ends.

Returning to 1530, for the case where both dual actuators are not in faulty error state, method 1500 continues at 1540, where the controller 1750 determines if the non-quarantined (e.g., non-degraded) actuator changes state. Determining if the non-quarantined actuator changes state may be responsive to a triggering event, including one or more of a change in a user command state, a change in the actuator action state, and exceeding a threshold duration, as described above. In response to a change in the logic state of the non-quarantined, method 1500 continues at 1544 where the controller 1750 stores the dual actuator logic states before triggering a state transition from S2 to S3, to re-evaluate the status of the dual actuated input device 1798 including recalculating the truth table equation output. Furthermore, storing the logic states at 1544 may include storing the current dual actuator logic states in non-transitory memory at the controller 1750. In particular, the current (e.g., $N^{th}$) actuator logic states are stored as the $(N-1)^{th}$ historical logic states; and any preceding $(N-M)^{th}$ logic state stored in memory may be shifted and redesignated in memory to the $(N-M-1)^{th}$ logic state. Returning to 1540, for the case where the non-quarantined actuator does not change logic state, method 1500 continues at 1550 where the controller 1750 maintains the state S2 and operation of the dual actuator system.

Figure 16:
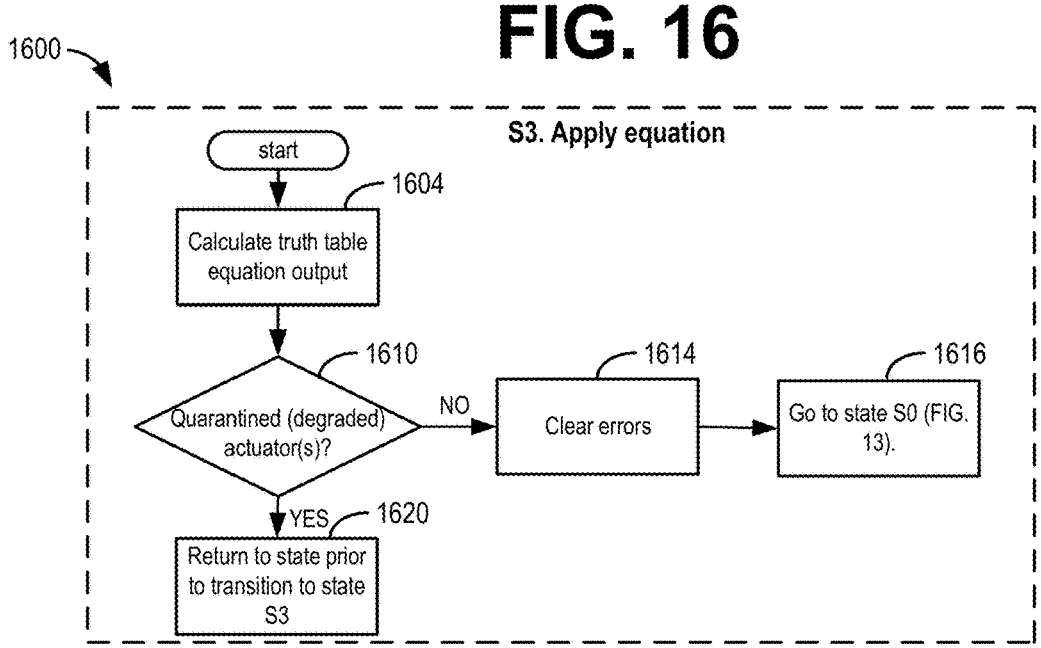

Turning now to FIG. 16, it illustrates a method 1600 including executable instructions corresponding to the state S3 of the state machine 1100. The state S3 corresponds to a state where the dual actuated input device 1798 is stable, and the truth table equation 1010 is calculated to reassess the status of the dual actuated input device 1798. Method 1600 begins at 1604 where the output of the truth table equation 1010 is recalculated. Next, method 1600 continues at 1610 where the controller 1750 determines if there are any quarantined (e.g., degraded) actuators. An actuator may be quarantined during the state S1, and its quarantined status may be sustained through state S2, prior to transitioning to the state S3. In contrast, neither of the dual actuators may be quarantined for the case where the transition to state S3 is triggered from state S0 or S1. If the controller 1750 determines that there are no quarantined actuators at 1610, method 1600 continues at 1614 where any error fault statuses associated with the dual actuators are cleared. Although the controller 1750 determines that there are no quarantined actuators at 1610, clearing any error fault statuses associated with the dual actuators at 1614 aids in reducing a risk of identifying a false fault status during a normal condition (e.g., no dual actuator faults) while in the state S3 by helping to ensure that any residual lingering false dual actuator faults due to system delays are removed. Subsequently, the controller 1750 triggers a transition from state S3 to state S0, indicating resumption of normal mode operation.

Returning to 1610, for the case where one or more quarantined actuators are indicated, method 1600 proceeds to 1620 where the controller 1750 triggers a transition returning to the state from which the transition to state S3 was made.

In this manner, one embodiment of a method for controlling an electronic system includes, at the electronic system, in response to receiving input at an input device, actuating a dual actuator and transmitting output signals from the dual actuator to a controller, converting the transmitted output signals to real-time logic states at the controller, inputting the real-time logic states to a programmable device of the controller, and determining a fault status of the dual actuators based on logic states input to the programmable device, wherein the logic states include the real-time logic states and historical logic states stored at the controller prior to inputting the real-time logic states to the programmable device. A first example of the method further includes wherein actuating the dual actuator in response to receiving the input at the input device includes actuating a first actuator, and actuating a second actuator before a threshold duration elapses after actuating the first actuator. A second example of the method, optionally including the first example, further includes wherein converting the transmitted output signals to logic states at the controller includes outputting a first logic state when the transmitted output signal is less than a lower threshold value and outputting a second logic state different from the first logic state when the transmitted output signal is greater than an upper threshold value. A third example of the method, optionally including one or more of the first and/or second examples, further includes wherein the threshold duration includes 1.5 s. A fourth example of the method, optionally including one or more of the first through third examples, further includes indicating an error fault status at one of the first and second actuators in response to the real-time logic state of the first actuator being equivalent to the real-time logic state of the second actuator, and maintaining operation of the input device in response to the indicated error fault status. A fifth example of the method, optionally including one or more of the first through fourth examples, further includes changing the error fault status indicated at one of the first and second actuators to a degraded status in response to the real-time logic state of the first actuator being equivalent to the real-time logic state of the second actuator persisting beyond the threshold duration, and maintaining operation of the input device in response to the indicated degraded status. A sixth example of the method, optionally including one or more of the first through fifth examples, further includes clearing the error fault status indicated at one of the first and second actuators in response to a change in the real-time logic state of the first actuator or the real-time logic state of the second actuator prior to the threshold duration.

In this manner one embodiment of a method of controlling an electronic system includes, at the electronic system, in response to receiving input at an input device, transmitting first and second output signals from first and second actuators, respectively, to a controller, the controller including a comparator and a programmable device, converting the first and second output signals to first and second real-time logic states, respectively, at the comparator, inputting the first and second real-time logic states from the comparator to the programmable device, and determining a fault status of the first and second actuators based on logic states input to a state machine of the programmable device, wherein the logic states input to the state machine include the first and second real-time logic states and historical logic states stored at the controller. A first example of the method further includes wherein determining the fault status of the electronic system based on the logic states input to the state machine includes indicating a normal mode during a first condition, including when the first and second real-time logic states are inequivalent. A second example of the method, optionally including the first example, further includes wherein determining the fault status of the first and second actuators based on the logic states input to the state machine includes indicating an error mode during a second condition, including when the first and second real-time logic states are equivalent. A third example of the method, optionally including one or more of the first and/or second examples, further includes wherein the historical logic states include a first historical logic state corresponding to the first actuator and a second historical logic state corresponding to the second actuator, and the second condition further includes when the first historical logic state is different from the first real-time logic state or when the second historical logic state is different from the second real-time logic state. A fourth example of the method, optionally including one or more of the first through third examples, further includes wherein the first condition further includes when the first historical logic state is different from the first real-time logic state or when the second historical logic state is different from the second real-time logic state. In another representation, a fifth example of the method, optionally including one or more of the first through fourth examples, further includes determining the fault status of the electronic system based on the logic states input to the state machine, wherein the logic states input to the state machine include an output logic state calculated based on the first and second real-time logic states and the first and second historical logic states. In another representation, a sixth example of the method, optionally including one or more of the first through fifth examples, further includes wherein the output logic state being equivalent to a first output logic state corresponds to an unactuated user command state, and the output logic state being equivalent to a second output logic state corresponds to an actuated user command state.

In this manner, one embodiment of an electronic system includes, a user interface comprising an input device, a first actuator and a second actuator, the first and second actuators dually actuated by the input device, and a controller, including a comparator, a programmable device, and executable instructions residing in non-transitory memory thereon to, receive first and second output signals from the first and second actuators, respectively, convert the first and second output signals to first and second real-time logic states at the comparator, input the first and second real-time logic states from the comparator to the programmable device, and determine a fault status of the first and second actuators based on the first and second logic states input to a state machine of the programmable device, wherein the first and second logic states input to the state machine include the real-time logic states and historical logic states stored at the controller. A first example of the electronic system further includes, wherein the historic logic states include logic states input to the programmable device from the comparator and stored at the controller prior to inputting the real-time logic state to the programmable device from the comparator. A second example of the electronic system, optionally including the first example, further includes, wherein the programmable device includes a field programmable gate array. A third example of the electronic system, optionally including one or more of the first and/or second examples, further includes, wherein the comparator includes an inverter with a Schmitt trigger. A fourth example of the electronic system, optionally including one or more of the first through third examples, further includes, wherein the first and second actuators include a dual switch. A fifth example of the electronic system, optionally including one or more of the first through fourth examples, further includes, wherein the executable instructions to transmit the first and second output signals from the first and second actuators, respectively, to the controller is in response to receiving user input at the input device. A sixth example of the electronic system, optionally including one or more of the first through fifth examples, further includes, wherein the controller includes a controller for a medical imaging system, and the input device includes a button for actuating motion control of the medical imaging system. A seventh example of the electronic system, optionally including one or more of the first through sixth examples, further includes a computing device remotely located from but communicatively coupled to the medical imaging system, wherein the computing device includes the controller.

In another representation, an embodiment of an electronic system includes, an input device, dual actuators, the dual actuators dually actuated by the input device, and a controller, including a comparator, a programmable device, and executable instructions residing in non-transitory memory thereon to, determine an error fault status of each of the dual actuators, in response to the error fault status of only one of the dual actuators being faulty, maintaining operation of the input device, and in response to the error fault status of both of the dual actuators being faulty, discontinuing operation of the input device and reporting an error to the operator. A first example of the electronic system further includes wherein the executable instructions to determine the error fault status of each of the dual actuators includes determining the error fault status of the dual actuators in response to a triggering event, the triggering event including a change in an action state of either of the dual actuators. A second example of the electronic system, optionally including the first example, further includes wherein the executable instructions to determine the error fault status of each of the dual actuators includes determining the error fault status of the dual actuators in response to a triggering event, the triggering event including exceeding a threshold duration since last determining the error fault status of the dual actuators. A third example of the electronic system, optionally including one or more of the first and/or second examples, further includes wherein the executable instructions further comprise, in response to the error fault status of one of the dual actuators being faulty, indicating a degraded actuator status corresponding to either of the dual actuators being faulty. A fourth example of the electronic system, optionally including one or more of the first through third examples, further includes wherein the executable instructions to determine the error fault status of each of the dual actuators includes determining the error fault status of each of the dual actuators based on real-time and historical logic states of the dual actuators. A fifth example of the electronic system, optionally including one or more of the first through fourth examples, further includes wherein determining the error fault status of each of the dual actuators further includes determining the error fault status of each of the dual actuators based on a truth table logic state, wherein the truth table logic state is calculated from the real-time and historical logic states of the dual actuators. A sixth example of the electronic system, optionally including one or more of the first through fifth examples, further includes executable instructions to calculate the truth table logic state, including outputting a first truth table logic state during a condition when a user command state of the input device is unactuated, and outputting a second truth table logic state during a condition when the user command state of the input device is actuated. A seventh example of the electronic system, optionally including one or more of the first through sixth examples, further includes wherein the executable instructions to determine the error fault status of each of the dual actuators includes determining the error fault status of each of the dual actuators in response to a triggering event, the triggering event including receiving a rising or falling signal edge output from either of the dual actuators. An eighth example of the electronic system, optionally including one or more of the first through seventh examples, further includes wherein the executable instructions to determine the error fault status of each of the dual actuators includes determining the error fault status of each of the dual actuators in response to a triggering event, the triggering event including receiving a new output signal transmitted from the first or second actuator. A ninth example of the electronic system, optionally including one or more of the first through eighth examples, further includes wherein the executable instructions further comprise, in response to a change in the logic state of one of the dual actuators having the degraded actuator status, changing the degraded actuator status to a non-degraded actuator status.

In another representation, an embodiment of a method of operating a dually actuated electronic system includes, actuating dual actuators in response to user input at an input device, determining an error fault status of each of the dual actuators, in response to the error fault status of at least one of the dual actuators being non-faulty, maintaining operation of the input device, and in response to the error fault status of both of the dual actuators being faulty, discontinuing operation of the input device and reporting an error to the operator. A first example of the method further includes, wherein determining the error fault status of each of the dual actuators includes inputting logic states corresponding to each of the dual actuators to a state machine and calculating a truth table output logic state, wherein determining the error fault status of each of the dual actuators includes determining a truth table output logic state based on the logic states corresponding to each of the dual actuators. A second example of the method, optionally including the first example, further includes, wherein determining the error fault status of each of the dual actuators includes inputting the truth table output logic state and the logic states corresponding to each of the dual actuators to a state machine and performing a state machine analysis. A third example of the method, optionally including one or more of the first and/or second examples, further includes, wherein performing the state machine analysis includes, during a first state condition, in response to the logic states of each of the dual actuators being equivalent, indicating an error fault status at one of the dual actuators and entering a second state condition. A fourth example of the method, optionally including one or more of the first through third examples, further includes, wherein performing the state machine analysis includes, during the first state condition, indicating a short circuit fault between the dual actuators in response to a real-time logic state being inequivalent to a historical logic state for each of the dual actuators. A fifth example of the method, optionally including one or more of the first through fourth examples, further includes, wherein during a second state condition, indicating the error fault status at one of the dual actuators is further in response to a threshold time elapsing after determining the logic states of each of the dual actuators being equivalent. A sixth example of the method, optionally including one or more of the first through fifth examples, further includes, during the second state condition, resetting the threshold time in response to a change in the logic state of one of the dual actuators changing prior to the threshold time elapsing. A seventh example of the method, optionally including one or more of the first through sixth examples, further includes, during the first state condition, indicating the error fault status at an idle actuator in response to a change in a logic state of an active actuator after the threshold time elapsing. An eighth example of the method, optionally including one or more of the first through seventh examples, further includes, during a third state condition, clearing the error fault status of one of the dual actuators in response to a change in the logic state of the one of the dual actuators. A ninth example of the method, optionally including one or more of the first through eighth examples, further includes, wherein the active actuator corresponds to one of the dual actuators undergoing a transition to a different logic state, and wherein the error fault status arises in response to the transition to the different logic state. A tenth example of the method, optionally including one or more of the first through ninth examples, further includes, wherein the idle actuator corresponds to one of the dual actuators maintaining a constant logic state during a conditions when one of the dual actuators undergoes the transition to the different logic state.

In this way the technical effect of increasing fault tolerance of a dually actuated control system as compared to conventional systems may be achieved. Furthermore the increased fault tolerant dually actuated control system may be provided without having a control system with dually redundant control hardware, thereby avoiding increased system complexity and cost. Further still, the electronic system described herein includes a method of assessing a severity and type of a fault such that in the case of certain less-severe fault types, functionality of the control system can be maintained. As such, the robustness and fault tolerance of the electronic system can be increased relative to conventional dual actuated systems. Moreover, in the case of medical systems such as control systems for interventional radiology imaging, increased robustness and fault tolerance can aid in reducing the occurrence and severity of medically undesirable consequences by reducing outright failures due to transient (less-severe) faults. Further still, a more robust fault tolerant control system can be provided while maintaining compliance with industry standards.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An electronic system including:
a user interface comprising an input device,
a first actuator and a second actuator, the first and second actuators dually actuated by the input device, and
a controller, including
a comparator,
a programmable device including a state machine, and
executable instructions residing in non-transitory memory thereon to,
receive first and second output signals from the first and second actuators, respectively,
convert the first and second output signals to first and second real-time logic states at the comparator,
input the first and second real-time logic states from the comparator to the programmable device, and
determine a fault status of the first and second actuators based on the first and second logic states input to the state machine, wherein the first and second logic states input to the state machine include the real-time logic states and historical logic states stored at the controller.

2. The electronic system of claim 1, wherein the historic logic states include logic states input to the programmable device from the comparator and stored at the controller prior to inputting the real-time logic state to the programmable device from the comparator.

3. The electronic system of claim 1, wherein the programmable device includes a field programmable gate array.

4. The electronic system of claim 1, wherein the comparator includes an inverter with a Schmitt trigger.

5. The electronic system of claim 1, wherein the first and second actuators include a dual switch.

6. The electronic system of claim 1, wherein the executable instructions to transmit the first and second output signals from the first and second actuators, respectively, to the controller is in response to receiving user input at the input device.

7. The electronic system of claim 1, wherein the controller includes a controller for a medical imaging system, and the input device includes a button for actuating motion control of the medical imaging system.

8. The electronic system of claim 7, further comprising a computing device remotely located from but communicatively coupled to the medical imaging system, wherein the computing device includes the controller.

9. A method for controlling an electronic system, including:
at the electronic system,
in response to receiving input at an input device, actuating a dual actuator and transmitting output signals from the dual actuator to a controller,
converting the transmitted output signals to real-time logic states at the controller,
inputting the real-time logic states to a programmable device of the controller, and
determining a fault status of the dual actuators based on logic states input to the programmable device, wherein the logic states include the real-time logic states and historical logic states stored at the controller prior to inputting the real-time logic states to the programmable device.

10. The method of claim 9, wherein actuating the dual actuator in response to receiving the input at the input device includes actuating a first actuator, and actuating a second actuator before a threshold duration elapses after actuating the first actuator.

11. The electronic system of claim 10, wherein converting the transmitted output signals to logic states at the controller includes outputting a first logic state when the transmitted output signal is less than a lower threshold value and outputting a second logic state different from the first logic state when the transmitted output signal is greater than an upper threshold value.

12. The method of claim 10, wherein the threshold duration includes 1.5 s.

13. The method of claim 10, further comprising
indicating an error fault status at one of the first and second actuators in response to the real-time logic state of the first actuator being equivalent to the real-time logic state of the second actuator, and
maintaining operation of the input device in response to the indicated error fault status.

14. The method of claim 13, further comprising
changing the error fault status indicated at one of the first and second actuators to a degraded status in response to the real-time logic state of the first actuator being equivalent to the real-time logic state of the second actuator persisting beyond the threshold duration, and
maintaining operation of the input device in response to the indicated degraded status.

15. The method of claim 13, further comprising clearing the error fault status indicated at one of the first and second actuators in response to a change in the real-time logic state of the first actuator or the real-time logic state of the second actuator prior to the threshold duration.

16. A method of controlling an electronic system, comprising:
at the electronic system,
in response to receiving input at an input device, transmitting first and second output signals from first and second actuators, respectively, to a controller, the controller including a comparator and a programmable device,
converting the first and second output signals to first and second real-time logic states, respectively, at the comparator,
inputting the first and second real-time logic states from the comparator to the programmable device, and
determining a fault status of the first and second actuators based on logic states input to a state machine of the programmable device, wherein the logic states input to the state machine include the first and second real-time logic states and historical logic states stored at the controller.

17. The method of claim 16, wherein determining the fault status of the electronic system based on the logic states input to the state machine includes indicating a normal mode during a first condition, including when the first and second real-time logic states are inequivalent.

18. The method of claim 17, wherein determining the fault status of the first and second actuators based on the logic states input to the state machine includes indicating an error mode during a second condition, including when the first and second real-time logic states are equivalent.

19. The method of claim 18, wherein
the historical logic states include a first historical logic state corresponding to the first actuator and a second historical logic state corresponding to the second actuator, and
the second condition further includes when the first historical logic state is different from the first real-time logic state or when the second historical logic state is different from the second real-time logic state.

20. The method of claim 19, wherein the first condition further includes when the first historical logic state is different from the first real-time logic state or when the second historical logic state is different from the second real-time logic state.

* * * * *